US006013823A

United States Patent [19]
Mamarella et al.

[11] Patent Number: 6,013,823
[45] Date of Patent: Jan. 11, 2000

[54] TRANS-PENTAVALENT 2-15-DEOXY-16-HYDROXY-16-METHYL-PGE1 METHYL ESTER (B-407)

[75] Inventors: Carlos Alberto Genaro Mamarella; Carlos Alberto Buschi; Silvia Susana Giarcovich, all of Buenos Aires, Argentina

[73] Assignee: New Pharma International Corp., Montevideo, Uruguay

[21] Appl. No.: 08/903,782

[22] Filed: Jul. 31, 1997

Related U.S. Application Data

[63] Continuation of application No. 08/072,188, Jun. 4, 1993, Pat. No. 5,817,694.

[30] Foreign Application Priority Data

Jun. 8, 1992 [CL] Chile .......................................... 570-92

[51] Int. Cl.[7] ...................................................... C07F 7/08
[52] U.S. Cl. ............................................................ 556/443
[58] Field of Search ............................................. 556/443

[56] References Cited

U.S. PATENT DOCUMENTS

| | | | |
|---|---|---|---|
| 4,190,597 | 2/1980 | Floyd, Jr. et al. | 556/427 |
| 4,529,812 | 7/1985 | Collins et al. | 560/121 |
| 4,617,411 | 10/1986 | Collins et al. | 556/443 |
| 5,166,174 | 11/1992 | Ueno et al. | 560/121 X |
| 5,705,659 | 1/1998 | Park et al. | 549/415 |

OTHER PUBLICATIONS

D. van Dorp, Recent Developments in the Biosynthesis and The Analyses of Prostaglandins, Unilever Research Laboratories Vlaardingen, The Netherlands, Annals New York Academy of Sciences, Editors, pp. 182–199.
Gilman, A.G. et al. (Eds.), The Pharmacological Basis of Therapeutics, 8th Edition, 1990, Chp. 24, pp. 600–617, 911, 937–939.
Von Priv.–Doz. Dr. H. Schmidbaur und cand. chem. Brunhilde Armer, Organogallogermoxane—Verbindungen mit der Struktureinheit Ga–O–Ge, Angew. Chem. 78 Jahrg, 1966, Nr. 5, pp. 305–306.
Sih, C.J., et al., Total Synthesis of (±)–15–Deoxyprostaglandin $E_1$, J.C.S. Chem. Comm., 1972, pp. 240–241.
Sammes, P.G., et al., On the Synthesis of Azetidines from 3–Hydroxypropylamines, J. Chem, Soc., Chem, Commun., 1983; pp. 682–684.
Ali, S.M., et al., Synthesis of Prostaglandin $A_2$ from 3–endo––Bromotricyclo [$3.2.0.0^{2.7}$] heptan–6–one, J.C.S. Chem. Comm., 1980, pp. 74–75.
Ali, S.M., et al., Synthesis of 9–Deoxa–9, 10–dehydroprostaglandin–$D_2$ through Reaction of 2–Oxatricyclo[$3.3.0.0^{4\,6}$] oct–7–en–3–one with a Cuprate Reagent, J.C.S. Chem. Comm. 1979, pp. 679–680.
Brown, E.A., et al., A Short Synthesis of Prostaglandins from 5–Chloro–5–cyano–7–syn–formylbicyclo[2,2,1] hept–2–ene, J.C.S. Chem. Comm. 1975, p. 39.

Dawson, M.J., et al., Reduction of Bicyclo [3.2.0] hept–2–en–6–one with Dehydrogenase Enzymes in Whole Cell Preparations of some Fungi and Yeasts, J. Chem Soc. Perkin Trans. I, 1983, pp. 2119–2125.
Jones, G., et al., Stero–controlled Synthesis of Prostaglandin Synthons, J.C.S. Perkin I, 1974, pp. 1676–1683.
Miller, J.G., et al., Highly Stereoselective Total Syntheses of Prostaglandins via Sterospecific Sulfenate–Sulfoxide Transformations, J. Amer. Chem. Soc., 96:21, Oct. 16, 1974, pp. 6774–6775.
Trost, B.M., et al., New Synthetic Reactions.Oxidative Decarboxylation, J. Amer. Chem. Soc., 97:12, Jun. 11, 1975, pp. 3528–3530.
Corey, E.J., et al., *Preparation of an Optically Active Prostaglandin Intermediate via Asymmetric Induction*, pp. 6908–6909.
Sih, C.J., et al., Total Synthesis of Prostaglandins II. Prostaglandin $E_1$, Communications to the Editor, J. Amer. Chem. Soc., 94:10, May 17, 1972, pp. 3643–3644.
Alvarez, F.S., et al., Synthesis of (±)–Prostaglandin $E_1$,(±)–11–Deoxyprostaglandins $E_1$, $F_1$, and (±)–9–Oxo–13–cis–Prostenoic Acid by Conjugate Addition of Vinylcopper Reagents, J. Amer. Chem. Soc. 94:22, Nov. 1, 1972, pp. 7823–7827.
Kluge, A.F., et al., Synthesis of Prostaglandin Models and Prostaglandins by Conjugate Addition of a Functionalized Organocopper Reagent, J. Amer. Chem. Soc., 94:22, Nov. 1, 1972, pp. 7827–7832.
Corey, E.J., et al., Efficient Generation of the 15S Configuration in Prostaglandin Synthesis, Attractive Interactions in Stereochemical Control of Carbonyl Reduction, J. Amer. Chem. Soc., 94:24, Nov. 29, 1972, pp. 8616–8618.
Roberts, S.M., et al., Factors Influencing the Regioselectivity of Reactions Involving Organocuprate Reagents and Allyl Acylates: Synthesis of Some Phenylthioprostanoids, J.C.S. Perkin I, 1981, pp. 1729–1733.
Iguchi, S, et al., Diisobutylaluminum 2,6–Di–t–butyl–4–methylphenoxide, Novel Stereoselective Reducing Atent for Prostaglandin Synthesis, Bull. Chem. Soc. Jpn., 54, 1981, pp. 3033–3041.
Noyori, R., Assymmetric Synthesis Via Axially Dissymmetric Molecules, A Binaphthol–Modified Complex Aluminum Hydride Reagent Possessing Extremely High Ability of Chiral Recognition, Pure & Appl. Chem., vol. 53, 1981, pp. 2315–2322.

(List continued on next page.)

*Primary Examiner*—Paul F. Shaver
*Attorney, Agent, or Firm*—Darby & Darby

[57] ABSTRACT

Analogs of the prostaglandin $PGE_1$ are disclosed. These compounds exhibit uterotonic properties, enhancing the response to $PGF_2\alpha$ in isolated rat uteri. The compounds also exhibit other pharmacological properties, as inhibitors of gastric acid secretion, hypotensives, and bronchodilators. Processes for making the analogs, useful intermediates, and pharmaceutical preparations are also presented.

2 Claims, No Drawings

OTHER PUBLICATIONS

Corey, E.J., et al., Stereo–Controlled Synthesis of Prostaglandins $F_{2\alpha}$ and $E_2$ (dl), J. Amer. Chem. Soc., 91:20, Sep. 24, 1969, pp. 5675–5677.

Corey, E.J., et al., Total Synthesis of Prostaglandins $F_{1\alpha}$, $E_1$, $F_{2\alpha}$, and $E_2$ (Natural Forms) from a Common Synthetic Intermediate, J. Amer. Chem. Soc., 92:8, Apr. 22, 1970, pp. 2586–2587.

Corey, E.J., et al., Studies on the Total Synthesis of Gibberellic Acids, A Simple Route to the Tetracarbocyclic Network, J. Amer. Chem. Soc., 92:2, Jan. 28, 1970, pp. 396–397.

Finch, M.A.W., et al., Synthesis of Prostaglandin $A_2$ through Reaction of 3–endo–Bromo–tricyclo[3.20.0$^{2.7}$] heptan–6–one with a Cuprate Reagent, J.C.S. Perkin I, 1981, pp. 1725–1728.

Chapleo, C.B., et al., Total Synthesis of Prostaglandin $A_2$ involving the Reaction of a Heterocuprate Reagent with an Allyl Epoxide, J.C.S. Perkin I, 1980, pp. 2084–2087.

Horsewood, P., et al., Preparation and Dienophilic Reactions of Nitrosyl Cyanide, J.C.S. Perkin I, 1980, pp. 1587–1591.

Howard, C.C., et al., Total Synthesis of Prostaglandin–$F_{2\alpha}$ involving Stereocontrolled and Photo–induced Reactions of Bicyclo[3.2.0]hepatones, J.C.S. Perkin I, 1980, pp. 852–857.

Lee, T.V., et al., Preparation and Some Reactions of 3–endo–Substituted Tricyclo[3 2.0.0$^{2.7}$]heptan–6–ones, J.C.S. Perkin I, 1978, pp. 1179–1182.

Lee, T.V., et al., Total Synthesis of Prostaglandin–$F_{2\alpha}$ through Homoconjugate Addition of an Organocuprate Reagent to a Tricyclo[3.2.0.0$^{2.7}$]heptanone, J.C.S. Perkin I, 1978, pp. 1176–1178.

Brown, E.D., et al., The Acetoxyfulvene Synthesis of Prostaglandins. Part I. synthesis of the Corey Aldehyde, J.C.S. Perkin I, 1978, pp. 1507–1510.

Noyori, R., et al., A Highly Efficient Synthesis of Prostaglandin Intermediates Possessing the 15S Configuration, J. Amer. Chem. Soc., 101:19, Sep. 12, 1979, pp. 5843–5844.

Corey, E.J., et al ., New Reagents for Stereoselective Carbonyl Reduction. An Improved Synthetic Route to the Primary Prostaglandins, J. Amer. Chem. Soc., 93:6, Mar. 24, 1971, pp. 1491–1493.

Corey, E.J., et al., A New Method for the 1,4 Addition of the Methylenecarbonyl Unit (–CH$_2$CO–) to Dienes, J. Amer. Chem. Soc., 93:17, Aug. 25, 1971, pp. 4326–4327.

Spurlock, L.A., et al., The Nature of the Carbonium Ion. VII. The Dehydronorbornyl Cations from Thiocyanate Isomerizations, J. Amer. Chem. Soc., 93:1, Jan. 13, 1971, pp. 146–151.

House, H.O., et al., The Chemistry of Carbanions. XII. The Role of Copper in the Conjugate Addition of Organometallic Reagents, The Chemistry of Carbanions, XII, Oct. 1966, pp. 3128–3141.

Kluge, A.F., et al., Synthesis of 13–cis–Prostaglandins via a Highly Stereoselective Conjugate Addition with a Functionalized Organocopper Reagent, J. Amer. Chem. Soc., 94:26, Dec. 27, 1972, pp. 9256–9258.

Corey, E.J., et al., Mixed Cuprate Reagents of Type $R_1R_2$ CuLi Which Allow Selective Group Transfer, J. Amer. Chem. Soc., 94:20, Oct. 4, 1972, pp. 7210–7211.

Corey, E.J., et al., Total Synthesis of Prostaglandins $E_2$ $F_{2\alpha}$ (dl) Via a Tricarbocyclic Intermediate, Tetrahedron Letters No. 4, 1978, pp. 307–310.

Just, G., et al., A Prostaglandin Synthesis, Tetrahedren Letters No. 22, 1967, pp. 2093–2097.

Cameron, A.G., et al., Total Synthesis of Prostaglandin $D_1$ Methyl Ester and 9–EPI–Prostaglandin $D_1$ Methyl Ester, Tetrahedron Letters vol. 23, No. 5, 1982, pp. 561–564.

K. Kiec–Kononowicz et al., Reaction of 5,5–diphenyl–2–thiohydantoin with 1,3–dibromopropane Under Phase Transfer Catalytic Conditions, Tetrahedron vol. 37, 1981, pp. 409–415.

Lish, P.M., et al., Pharmacology of Methdilazine (Tacaryl$^{(R)}$), Arch int. pharmacodyn., CXXIX, No. 1–2, 1960, pp. 77–107.

Suzuki, M., et al., A General Synthesis of Primary Prostaglandins, Tetrahedron Letters, vol. 23, No. 52, 1982, pp. 5563–5566.

Nelson, N.A., Prostalandin Nomeclature, Journal of Medicinal Chemistry, 1974, vol. 17, No. 9, pp. 911–918.

Takano, S., et al., A New Prostaglandin Synthon from the 4–Oxatricyclo[4.3.0.0$^{3.7}$]non–8–ene System. A Total Synthesis of (±)–Prostaglandin $F_{2\alpha}$, Chem. Pharm. Bull. 27(11) 1979, pp. 2582–2588.

Peel R., et al., An Alternative Synthesis of the Corey Prostaglandin Aldehyde, J.C.S. Chem. Comm., 1974, pp. 151–153.

Dajani, E.Z., et al., Effects of E Prostaglandins, Diphenoxylate and Morphine on Intestinal Motility In Vivo, European Journal of Pharmacology, 34, 1975, pp. 105–113.

Dunham, N.W., et al., A Note on a Simple Apparatus for Detecting Neurological Deficit in Rats and Mice, J. Amer. Pharm. Assoc., vol. XLVI, No. 3, Scientific Edition, Mar. 1957, pp. 208–210.

Armitage, A.K., et al., Thioxanthines with Potent Bronchodilator and Coronary Dilator Properties, Brit. J. Pharmacol., 16, 1961, pp. 59–76.

Litchfield, Jr., J.T., et al., A Simplified Method of Evaluating Dose–effect Experiments, J. Pharm. Exp. Ther., 96, 1949, 99–113.

Caton, M.P.L., et al., Synthesis of Classical Prostaglandins, in Chemistry of the Prostaglandins and Leukotrienes, Advances in Prostaglandin, Thromboxane, and Leukotriene Research, vol. 14, 1985, pp. cover, 73–129.

TRANS-PENTAVALENT 2-15-DEOXY-16-HYDROXY-16-METHYL-PGE1 METHYL ESTER (B-407)

This is a division of application Ser. No. 08/072,188, filed Jun. 4, 1993, now U.S. Pat. No. 5,817,694.

Priority is claimed from Chilean application no. 570-92, filed Jun. 8, 1992.

SUMMARY OF THE RELATED ART

Review: The product described in the present invention is a $PGE_1$ analog. Natural prostaglandins are alicyclic compounds related to the prostanoic acid structure (Formula II).

It is useful to bear in mind the following statements related to natural products connected chemically and biologically to the molecule described in this invention.

Eicosanoids: Are biologically active substances derived from polyunsaturated C-20 fatty acids and include prostaglandins and leukotrienes.

Prostanoids: Are metabolic products derived from polyunsaturated fatty acids, mainly arachidonic acid (III). This transformation is catalyzed by the fatty acid cyclooxygenase-peroxidase. These compounds are extremely potent mediators of a diverse group of physiologic processes.

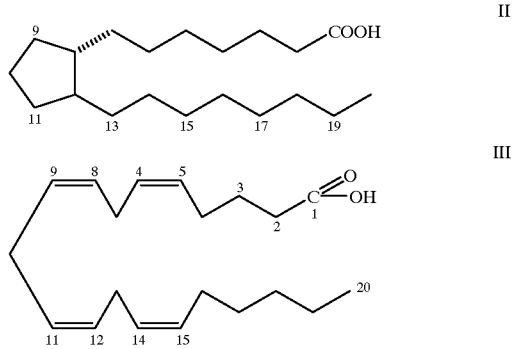

Natural prostaglandins: Are related to prostanoic acid (II) and result of either reductive or disproportionate cleavage of the peroxy linkage of the endoperoxide products produced by the fatty acid cyclooxygenase-peroxidase.

In natural prostaglandins, positions 13 and 14 are bonded by a trans double bond and position 15 has a hydroxyl group with alpha configuration.

The upper side chain is attached to a cyclopentane ring with α configuration (below the ring plane) and the lower side chain has a β configuration (above the ring plane). Both chains has a trans configuration with respect to the cyclopentane ring.

Prostaglandins have different substituents, in the cyclopentane ring and are classified according to the substitution on the cyclopentane ring and according to the number of double bonds present in the upper and lower side chains. In accordance with the substitution on the cyclopentane ring, different types of prostaglandins are obtained. A, E, F, G, I and J (FIG. A).

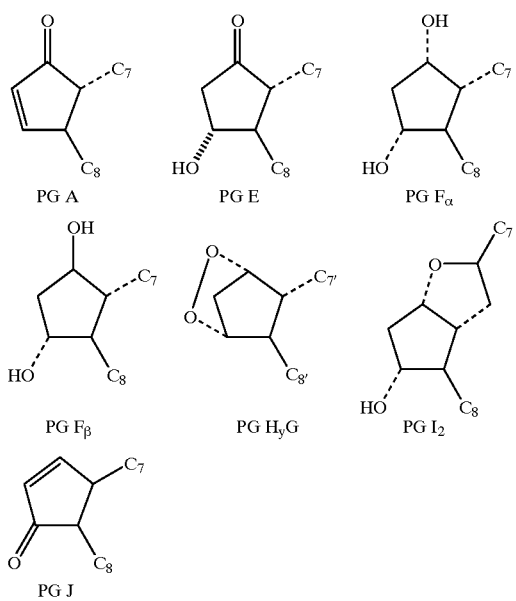

The distinction between prostaglandins A and G lies outside the cyclopentane ring. Prostacycline or $PGl_2$ has an additional oxolane ring (an ether linkage from C-9 to C-6) but nonetheless is considered as prostaglandin and can be named as a 6,9-α-oxoprostanoic acid derivative.

The location and number of double bonds between $C_5$–$C_6$; $C_{13}$–$C_{14}$ and $C_{17}$–$C_{18}$ defined three subtypes of prostaglandins.

A trans-double bond at $C_{13}$–$C_{14}$ defines the series 1 (IV) and is indicated by a subscript 1 written below the letter that defines the prostaglandin type (ie: prostaglandin $A_1$ or $PGA_1$).

The presence of both a trans-double bond at $C_{13}$–$C_{14}$ and a cis-double bond at $C_5$–$C_6$ define series 2 Prostaglandins (V) and is indicated with a subscript 2 (ie: $PGE_2$).

Finally, a trans-double bond at $C_{13}$–$C_{14}$, a cis-double bond at $C_5$–$C_6$ and a cis-double bond at $C_{17}$–$C_{18}$, define the series 3 (VI) and is indicated with a subscript 3.

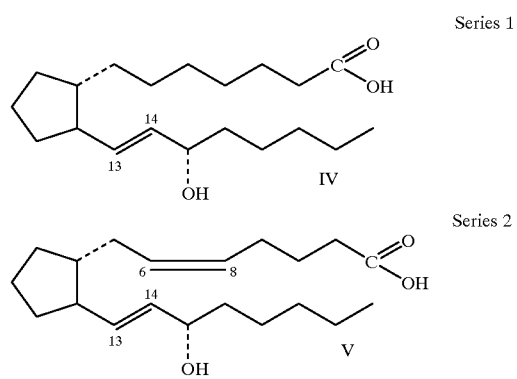

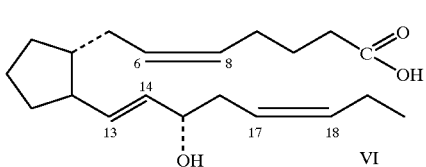

Series 3

VI

This nomenclature, based on type and series definition uses trivial names of prostaglandins and designates analogs by modification of the trivial names [J.Med. Chem. 17, 911 (1974)].

Another system follows rules of the "International Union of Pure an Applied Chemistry" (IUPAC) or the "Chemical Abstracts" (CA). The first one names prostaglandins as derivatives of heptanoic acid and the second one as derivatives of prostanoic acid.

The trivial name of structure VII is prostaglandin $F_1$ or $PGF_{1\alpha}$ in the IUPAC system: 7-[3R,5S-dihydroxy-2R-(3S-hydroxy-1E-octenyl)-cyclopent-1R-yl] heptanoic acid and in the CA system: (9α, 11α, 13E, 15S)-9,11,15-trihydroxy-prost-13-en-1-oic acid.

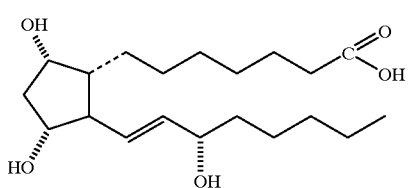

VII

The Cahn-Ingold-Prelog system [(Agnew. Chem. Int. Ed. Engl. 5, 385 (1966)] defines the stereochemistry of any asymmetric center and the α,β designation of the asymmetric carbons is still in use.

The double bond configuration is designed by the use of prefixed cis or trans or the equivalents Z or E.

Prostaglandins have ubiquitous distribution in animal tissues and promote both physiological and pathophysiological effects in mammals. They have diverse pharmacological effects on the cardiovascular system, gastrointestinal, circulatory and smooth muscle.

Prostaglandins E and A are potent vasodilators for most species and in most vascular beds (except in big veins) where $PGF_{2\alpha}$ shows greater species variation. PGE's and PGA's initially lower arterial blood pressure and consequently the peripheral resistance. This action promotes an increase of the cardiac output and organs blood flow.

$PGE_1$, $PGD_2$ (0.1 μM) and $PGI_2$ (1 to 10 nM) inhibit platelets aggregation "in vitro". PGA, $PGE_1$ and $PGE_2$ induce erythropoietin release from the kidney cortex producing an increase on the erythropoiesis.

The effects of prostaglandins on smooth muscle are diverse: $PGE_2$ and $PGI_2$ inhibit histamine release from basophilic leukocytes. Prostaglandins of the F series contract tracheal and bronchial smooth muscle whereas prostaglandins E relax these muscles.

$PGI_2$ is hypotensive for most species, including humans. PGF's type contract human non-pregnant uterine smooth muscle strips whereas prostaglandins type A, E and B relax these muscles.

PGF and $PGE_2$, at low concentrations, contract pregnant uterine muscle strips while $PGI_2$ and high concentrations of $PGF_2$ relax the uterine muscle. The intravenous administration of either $PGE_2$ or $PGF_{2\alpha}$ produces a dose-dependent increase of the frequency and intensity of the contraction of the pregnant human uterus. Some prostaglandins induce cervical ripening and softening when locally administered.

Prostaglandins of E and F series contract the longitudinal muscle "in vitro" from the stomach to the colon whereas PGF contracts and PGE relaxes circular smooth muscle.

The administration of PGE causes diarrhea, cramps, biliary reflux and nausea when administered as abortifacient for the termination of pregnancy.

Finally, prostaglandins E and $I_2$ inhibit both the gastric acid and pepsin secretion stimulated by feeding, histamine, acetylcholine- and gastrin-induced secretions. Prostaglandins also increase both mucous, water and the electrolytes secretion from the digestive tract. This results in diarrhea and abdominal cramps, often at therapeutic dosages.

As a consequence of their multiple pharmacological effects, prostaglandins and their analogs have broad and diverse therapeutic uses. PGE's and PGF's may be used in obstetric and gynecology for abortion and labor induction. In gastroenterology they are used either to treat peptic ulcers or disorders involving motility, secretion or absorption in the gastrointestinal tract. They are also useful bronchodilators, as anticlotting agents and for the treatment of circulatory diseases such as hypertension, peripheral vascular diseases and cardiac disorders.

There are more complete information related to the properties and actions of these compounds in the following references: [Ann. N. Y. Acad. Sci., 180:1 (1971); J. Am. Med. Assn., 53: 92 (1972); "Prostaglandinas y Compuestos Relacionados" (1989), El Ateneo Ed., Bs. As.; "The Pharmacological Basis of Therapeutics" (1990), Gillman, Rall, Nies, Taylor Eds., Pergamon Press, New York].

Until now, no $PGE_1$ analog was introduced to human therapeutics for the induction of labor at term. Listed below are all available data on prior art that are relevant to this invention:

A) The first prior art to consider in the present patent refers to the drugs employed with the objective of stimulating the uterine contractions in the following clinical settings: a) induction or promotion of labor, b) control of postpartum bleeding and uterine atonia, c) inducing uterine contractions after a cesarean section or during uterine surgery and d) induction of therapeutic abortions. The drugs more frequently employed for some of these uses are: oxytocin, $PGF_2$ and 15-methyl $PGF_{2\alpha}$.

In clinical studies, the usefulness of oxytocin and $PGE_2$ in patients with premature rupture of membranes and unripe cervix (Bishop score not higher than 6) was evaluated.

In general, the efficacy of both treatments were similar, but the period of labor induction is higher for $PGE_2$. However, either oral or intravaginal administration of $PGE_2$ are usually better accepted by the patients than intravenous oxytocin. The adverse effects were dose-dependent and compound-dependent. In newborn vaginally delivered fetuses, $PGE_2$ vaginal suppositories lowered umbilical artery blood pH values while oxytocin administration produced a higher incidence of fetal distress [Br. Med. J. 299, 1423 (1989); Arch. Gynaecol. Obstet. 247, 15 (1990); Eur. J. Obstet. Gynaecol. Reprod. Biol. 37 (2), 111 (1990); Obstet. Gynaecol 77 (2), 297 (1991); Ugeskr-Laeger 152 (49), 3705 (1990); Int. J. Gynaecol. Obstet. 33 (2), 115 (1990); Indian J. Med. Res. 90, 453 (1989)].

$PGE_1$ and $PGE_2$ analogs have been disclosed as abortifacients for pregnancy termination.

The PGE₁ analogs, misoprostol and gemeprost, are discussed in sections B and C described below. Other PGE₂ analogs, such as 15-(S) methyl PGE₂ and sulprostone are in different stages of clinical development [Br. J. Obstet. Gynaecol. 96 (12), 1400(1989); Geburtsh. Frauenheilkd. 47, 324 (1987); Contraception 39 (5), 497 (1989); Human Reproduction 4 (1), 21 (1989); Human Reproduction 4 (6) 718 (1989); Br. J. Obstet. Gynaecol. 87, 287 (1980)].

The therapeutic goal disclosed for the present invention for the drug code named B-407 is for the induction of labor at term. Thus, taking into account the above mentioned prior art, it can be concluded that no PGE₁ analogs are, at present, commercially available for human therapeutics.

B) Another prior art for the present patent is the U.S. Pat. No. 4,052,512 (ONO Pharm. Co., Ltd.) where a PGE₁ analog is disclosed. Its chemical name is 16,16-dimethyl-trans-$\Delta^2$-PGE₁ methyl ester (VIII). It is commercially known under the generic name gemeprost (ONO-802) and its structural formula (VIII) is shown below:

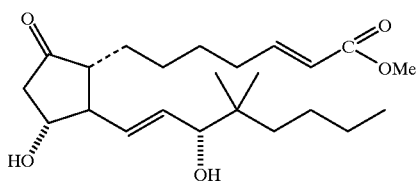

VIII

Gemeprost belongs to the natural series of the 15-hydroxy-prostaglandins and has a double bond between $C_2$ and $C_3$. Its principal use is as cervical softener but has been used to terminate first and second trimester pregnancy (therapeutically advised or not). Three or four suppositories of 1 mg of gemeprost administered at regular intervals have provoked complete abortions in more than 90% of the patients in various studies. Adverse effects consisting of abdominal pain, bleeding and gastrointestinal discomfort, nausea and vomiting are frequently observed with this drug. The main use of gemeprost is for cervical dilation before surgery in non-pregnant patients [Drugs of the Future 4 (1), 38 (1979); Adv. Contracept. 1 (1), 91 (1985); Prostaglandins 34 (1), 111 (1987); Br. J. Obstet. Gynaecol. 95 (3), 271 (1988); Contraception 39 (5), 497 (1989); Clin. Exp. Obstet. Gynaecol. 16, 61 (1989); Acta Obstet. Gynaecol. Scand. Suppl. 149, 13 (1989); Asia-Oceania J. Obstet. Gynaecol. 16 (1), 21 (1990); Br. J. Obstet. Gynaecol. 97 (6), 480 (1990)]. The clinical use disclosed in the present patent for B-407 is for labor induction at term. This use is absolutely different than that proposed for gemeprost which actually is for inducing cervical dilations and abortions.

C) Another prior art for the present patent is the U.S. Pat. No. 3,965,143 assigned to Searle & Co. where a PGE₁ analog is disclosed. Its chemical name is 15-deoxy-16-hydroxy-16-methyl PGE₁ methyl ester (IX). It is commercially available as misoprostol (Cytotec®) and its structural formula is shown below:

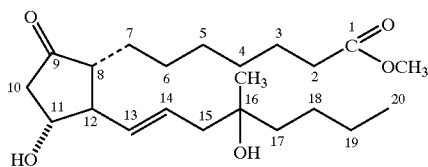

IX

Misoprostol does not belong to the natural series of the 15-hydroxy prostaglandins but it is a 15-deoxy-16-hydroxy prostaglandin which also has a methyl group in position 16. This compound is therapeutically employed as an antiulcer drug for the prevention of NSAID induced ulcers. Misoprostol in general, promotes the gastroduodenal mucosal defense after noxious of necrotizing agents [Gastroenterol-Nurs. 13 (1), 37 (1990); Am. J. Gastroenterol. 85 (11), 1498 (1990); Clin. Pharm. 8 (9), 627 (1989)].

Although misoprostol has better pharmacological specificity as antiulcer drug than most synthetic PGE analogs, however, in some instances, misoprostol can complicate or worsen abdominal side effects in patients with non-ulcer dyspepsia, prepyloric erosive changes or Crohn ileocolitis [Scand. J. Gastroenterol. 25 (10), 1028 (1990); Ann. Intern. Med. 113 (6), 474 (1990)].

It is interesting to note that the product disclosed by Searle is employed for therapeutic and commercial aims absolutely different than those described for B-407. In fact, misoprostol is prescribed only as an anti-ulcer drug. Other pharmacological properties disclosed in misoprostol patent are: as inhibitor of blood platelet aggregation, as bronchodilator and abortifacient. Thus, it cannot be used in pregnant women. Its principal adverse effects are diarrhea and abdominal cramps. Recently misoprostol has been recommended for use with mifepristone for the induction of abortion in the first trimester of pregnancy. [Lancet (1991) 338, 1233 (1991) and ibid. 338, 1241 (1991)].

D) Other related synthetic PGE₁ analogs are described in the literature as detailed below:

a) Prior art disclosed by Searle related to 3 oxaprostaglandins (EP 0115844). Antisecretory and cytoprotective properties are described for this compound and it is claimed for gastric ulcers treatment, abortifacient, inhibitior of blood platelet aggregation and bronchodilator.

b) The patent assigned to Miles Lab. (U.S. Pat. No. 4,331,688) which refers to PGE₁ analogs.

These compounds are claimed to be inhibitors of the gastric secretion with less side effects than misoprostol and have bronchodilator properties.

c) A patent assigned to Searle & Co. (U.S. Pat. No. 3,965,143) which claims that derivatives of 16-hydroxy prostanoic acid are inhibitors of the acid gastric secretion and of platelet aggregation; they are also bronchodilators and contraceptives.

d) The patent assigned to American Cyanamid Co. (U.S. Pat. No. 4,061,672) deals with 9-hydroxy-13-trans prostanoic acid derivatives. These compounds are postulated to be active as bronchodilator, antiulcer and hypotensive agents.

The synthesis of prostaglandin analogs is a well-known art for specialists and allows obtaining different prostaglandins backbone by several pathways. There are at least four big synthetic methods according to the Pike and Morton scheme [Advances in Prostaglandin, Thromboxane and Leukotriene. Research Vol. 14, Chemistry of Prostaglandins and Leukotrienes, Ed. J. E. Pike and D. R. Morton Jr. Raven Press-New York 1985].

a) Cleavage of polycyclic intermediates.
b) Conjugate addition.
c) Cyclization of aliphatic precursors.
d) Prostaglandin interconversions.

The synthetic methods are described in the following section:

Proposal (a)

1) Norbornene based routes: in this method disclosed by Corey, the chiral centers at C-8, C-11 and C-12 were preformed in the Diels Alder adduct (XII), (Scheme 1).

These syntheses were extensively used and modified by Corey and other researchers [J. Am. Chem. Soc. 93, 148 (1971); J. Am. Chem. Soc. 92, 2586 (1970); J. Am. Chem. Soc. 92, 387 (1970); J. Am. Chem. Soc. 91 5675 (1969); J. Am. Chem. Soc. 93, 1491 (1971); J. Am. Chem. Soc. 93, 4326 (1971); J. Am. Chem. Soc. 97, 6908 (1975); J. Am. Chem. Soc. 97, 3528 (1975)].

The methods used to afford a high degree of stereo control are of interest in the reduction of the C-15 ketone (XVIII) to the C-15-(S) alcohol (XIX).

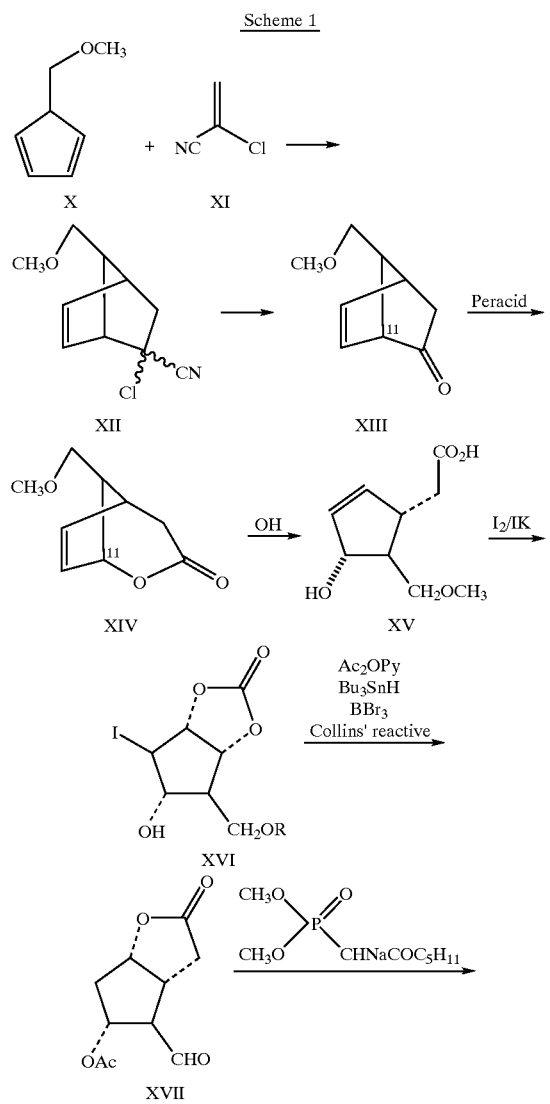

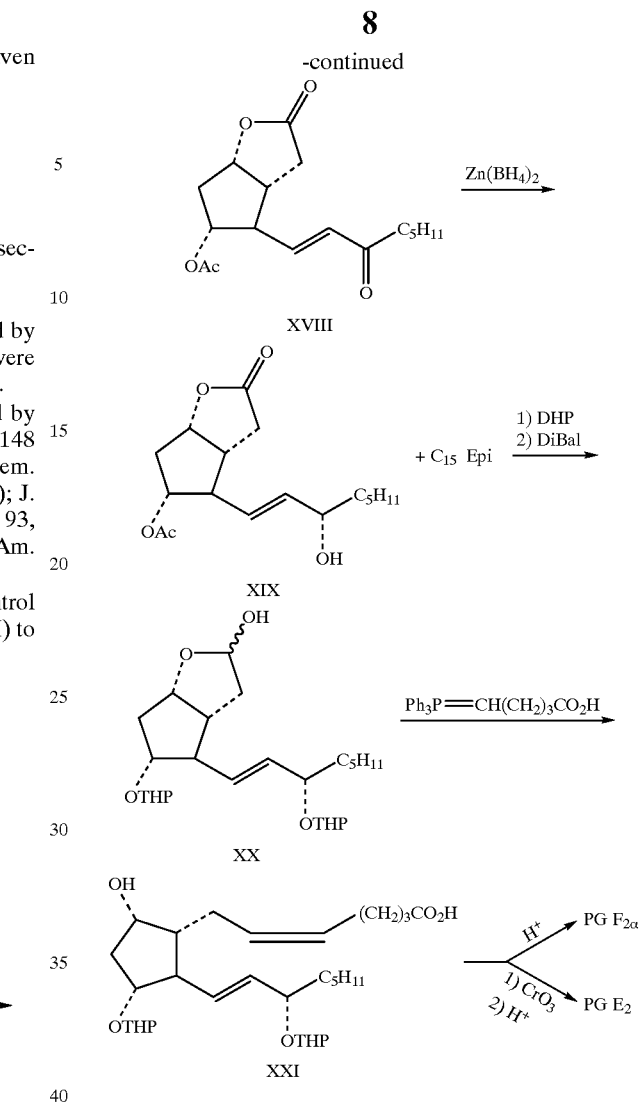

These are:

i) The use of a bulky borohydride as a reducing agent: Thexyl borane (+) limonene that was used in conjunction with p-nitrophenyl benzoyl attached to the C-11 cyclopentane ring oxygen as a directing group [J. Am. Chem. Soc. 94, 8616 (1972)].

ii) Diisobutylaluminum 2,6-di-t-butyl-4-methyl-phenoxide [Bull. Soc. J. 54, 3033 (1981)].

iii) Binaphthol aluminum hydride [Pure Appl. Chem. 53, 2315 (1981); J. Am. Chem. Soc. 101, 5843 (1979)].

This synthesis has been adapted to give $PGA_2$ and PGC series.

Later works done by ICI chemists have improved this already classical synthesis [J. Chem. Soc. (Perkin I) 1507 (1978); J. Chem. Soc. (Chem. Commun.) 39 (1975); Synth Commun 5, 221 (1975); J. Chem. Soc. (Perkin I), 1676 (1974); Tetrahedron Lett 23, 561 (1982); Tetrahedron 37, 411 (1981); J. Chem. Soc. Commun 151 (1974); Chem. Pharm. Bull. 9 (Tokyo) 27, 2582 (1979); Heterocycles 8 (1977)].

2) Bicycloheptanone approach: It was adapted from a Corey's idea [Tetrahedron Lett. 307 (1970)], by the Salford-Glaxo group (Scheme 2 and 3), that led to either $PGD_2$ or $PGF_{2\alpha}$ or $PGE_2$ in high yield. [J. Chem. Soc. (Perkin I) 2119 (1983); Chimia 14, 424 (1960); J. Chem. Soc. (Perkin I) 1176 (1978); J. Chem. Soc. (Perkin I) 1179 (1978)].

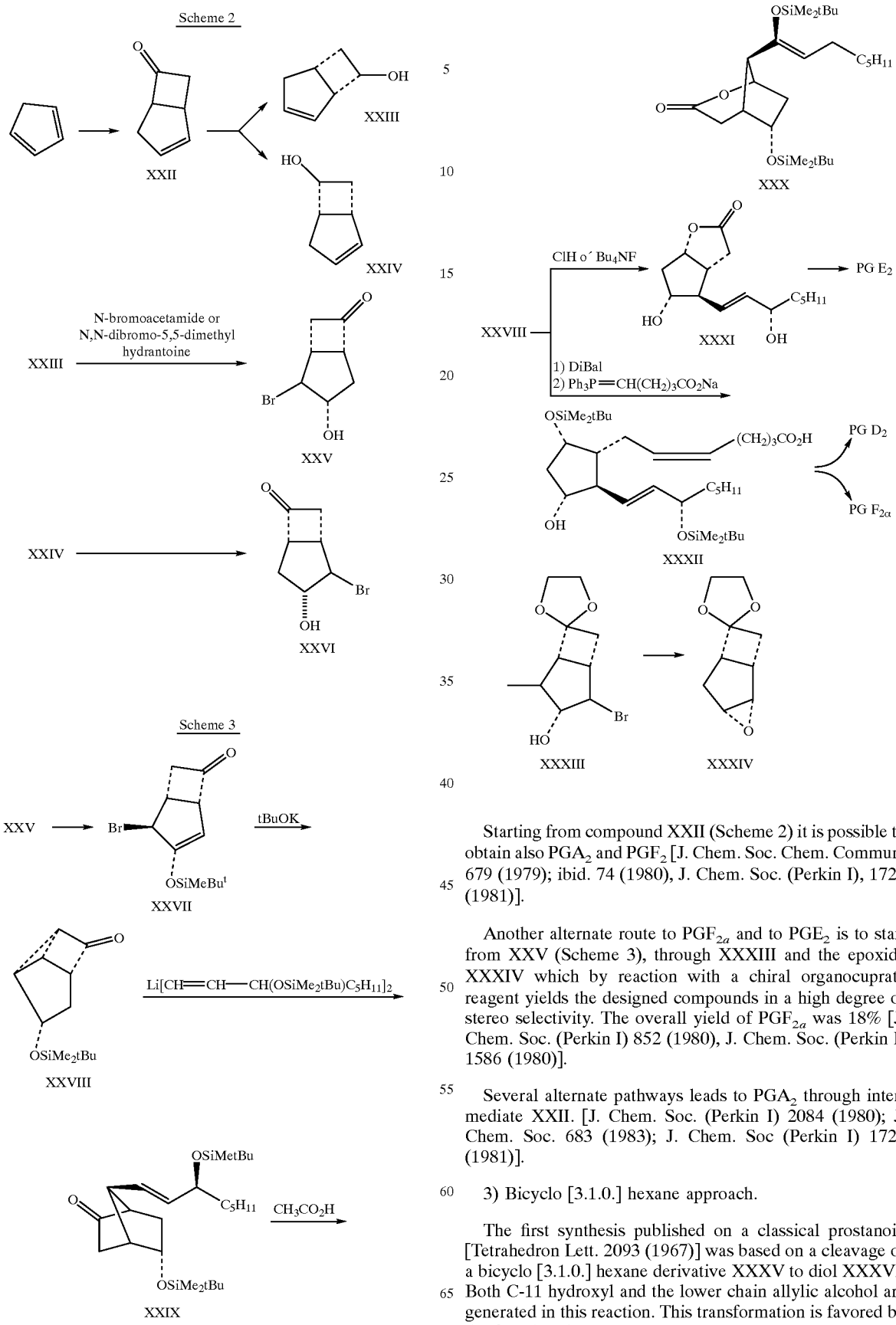

Starting from compound XXII (Scheme 2) it is possible to obtain also PGA$_2$ and PGF$_2$ [J. Chem. Soc. Chem. Commun. 679 (1979); ibid. 74 (1980), J. Chem. Soc. (Perkin I), 1725 (1981)].

Another alternate route to PGF$_{2\alpha}$ and to PGE$_2$ is to start from XXV (Scheme 3), through XXXIII and the epoxide XXXIV which by reaction with a chiral organocuprate reagent yields the designed compounds in a high degree of stereo selectivity. The overall yield of PGF$_{2\alpha}$ was 18% [J. Chem. Soc. (Perkin I) 852 (1980), J. Chem. Soc. (Perkin I) 1586 (1980)].

Several alternate pathways leads to PGA$_2$ through intermediate XXII. [J. Chem. Soc. (Perkin I) 2084 (1980); J. Chem. Soc. 683 (1983); J. Chem. Soc (Perkin I) 1729 (1981)].

3) Bicyclo [3.1.0.] hexane approach.

The first synthesis published on a classical prostanoid [Tetrahedron Lett. 2093 (1967)] was based on a cleavage of a bicyclo [3.1.0.] hexane derivative XXXV to diol XXXVI. Both C-11 hydroxyl and the lower chain allylic alcohol are generated in this reaction. This transformation is favored by the fact that the

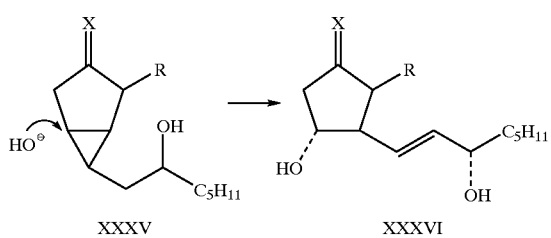

attack of the hydroxy ion is directed to the alpha orientation of C-11 whereas the trans-double bond formation is favored by the spatial disposition of the substituents during the ring opening sequence. This route has been extensively explored [Tetrahedron Lett. 1709 (1973); J. Am. Chem. Soc., 95 2746 (1973); Tetrahedron Lett. 1973 (1976); Tetrahedron Lett. 1753 (1976)].

4) Cyclohexane ring contraction approach:

It is possible to obtain compounds like Corey aldehyde derivatives XXXVIII from a tricyclic lactone XXXVII. In this case the cyclopentane ring is obtained by contraction of a cyclohexane derivative. [J. Am. Chem. Soc. 95, 6853 (1973); Tetrahedron Lett. 3091 (1973)].

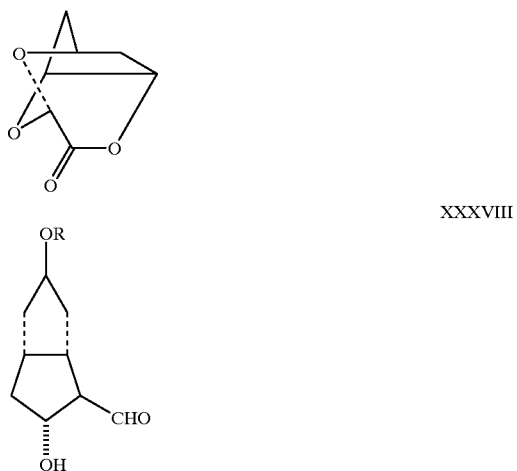

Proposal (b): Conjugate addition.

It is a highly convergent strategy. The key step of this approach is the formation of the $C_{12}$–$C_{13}$ carbon bond via a nucleophilic attack at the β-position of a protected cyclopentenone moiety.

The widespread use of the conjugate addition reaction in the synthesis of prostaglandins developed from the idea that the whole omega-chain could be attached to a cyclopentenone moiety via an organometallic derivative XL [J. Chem. Soc. Chem. Commun. 240 (1972)].

Scheme 4

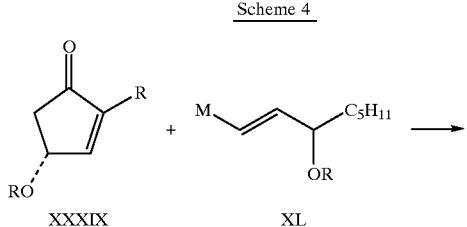

The conjugate addition yields all trans XLII (Scheme 4) since the hydrolysis of the intermediate enolate gives the thermodynamically more stable product and the attacking organometallic XL compound approach from the less hindered plane of the ring of the cyclopentenone XXXIX. It is important to have a bulky R group. In this way it is possible to obtain PGE derivatives in a totally stereospecific way.

Although a variety of organometallic reagents of structure XL have been shown to undergo conjugate addition reactions with α, β unsaturated ketones, work in this area was associated initially with the use of organocuprates which react exclusively to give 1,4-adducts; [J. Org. Chem. 31, 3128 (1966)].

The mechanism of the reaction is not completely known but it is assumed that one electron is transferred from the cuprate to the enone with the involvement of a Cu(III) species followed by a subsequent recombination of the copper radical cation with the enone radical anion. The final step is a reductive elimination that involves the transfer of the side chain to the β-position and enolate formation, precursor of XLVIII (Scheme 5).

A classical $PGE_1$ synthesis, using organocuprate reagents, was described independently by Sih's group and Syntex group, in 1972, using furil lithium as starting material [J. Chem. Soc. Chem. Commun. 240 (1972); J. Am. Chem. Soc. 94, 3643 (1972)] and by Fried [J. Am. Chem. Soc. 94, 7827 (1972)] Alvarex [J. Am. Chem. Soc. 94 7823 (1972)], see Scheme 5.

Although in the above mentioned references this synthesis was carried out using racemic materials, latter this approach included the preparation of chiral molecules of type L, new achiral protective groups developed and variations on the nature of the organometallic compound that greatly facilitated the synthesis and simplified the analytical work.

In the original Sih's work lithium cyclopentadienide was alkylated with ethyl bromoheptanoate which after cycloaddition with chemically generated singlet oxygen afforded a mixture of isomers XLIV and XLV (Scheme 5) containing the desired one (XLV) in less proportion. After Jones oxidation and posterior reduction with

Scheme 5

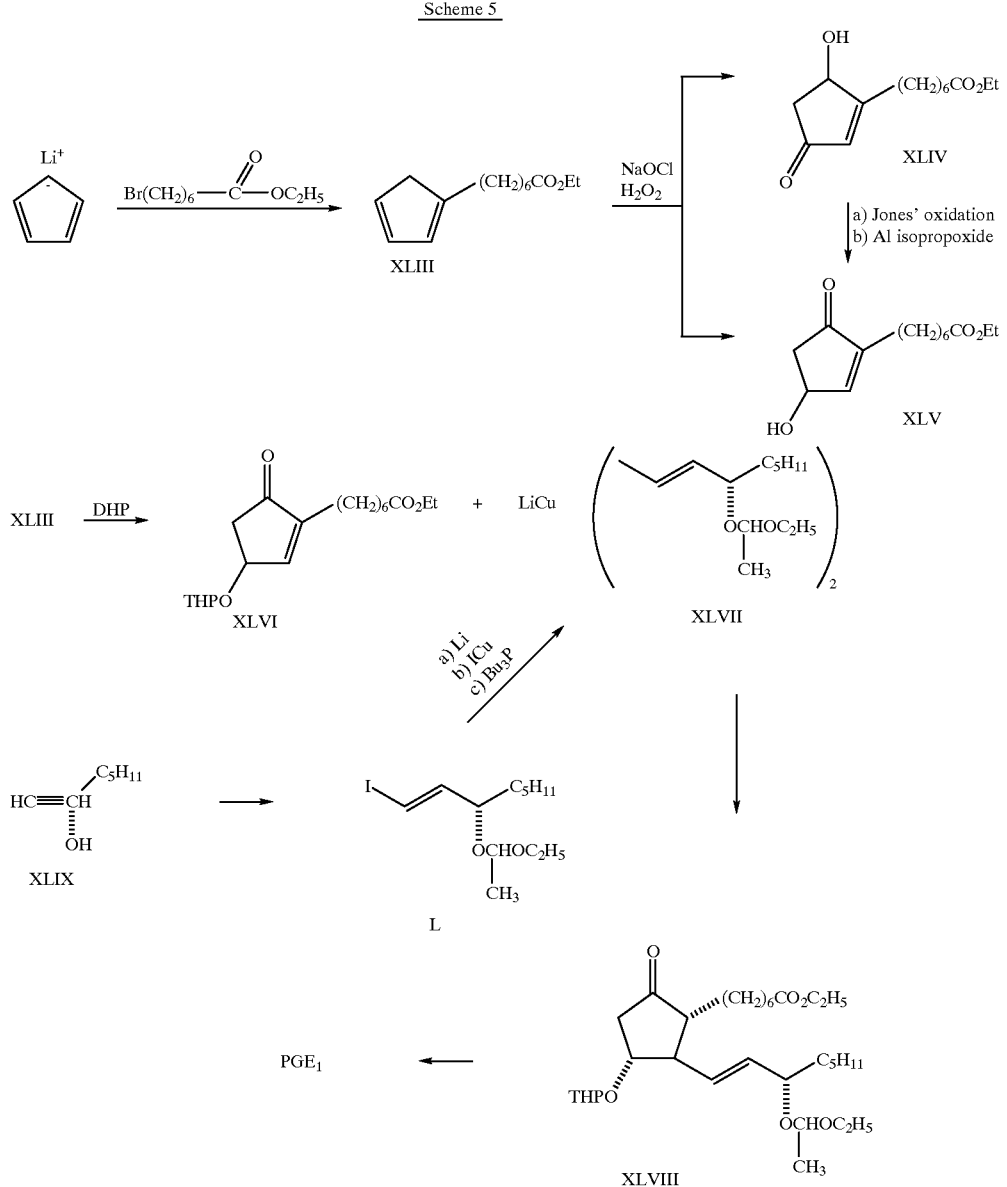

aluminium isopropoxide of the isomeric mixture, improved the isomer ratio to 2:1 in favor of XLV.

Organometallic compound nature:

Organocupric reagent of the divinyl cuprate type XLVII are formed by two R vinyl groups ($R_2Cu$: where R is the omega-chain). In an addition reaction, only one R group is transferred. As a result, the other group is not used, thus creating a serious problem, since the group is valuable owing to the difficulties to be obtained. To overcome this inconvenience, Corey suggested the use of mixed cuprate complex and vinyl cuprates, instead divinyl cuprates which are less reactive and give less side reactions [J. Am. Chem. Soc. 94, 7210 (1972)].

$R_r R_t Cu Li$ $R_r = CH_3CH_2CH_2C{\equiv}C{-}$

-continued $R_t =$ [structure with $OSi(Me)_2Bu^t$ and Li]

$R_t$ = group to be transferred
$R_r$ = residual group

Chiral cis vinyl cuprates was used instead of trans cuprates to give high yield of chiral addition products using racemic cyclopentenone as starting material [J. Am. Chem. Soc. 94, 9256 (1972); J. Am. Chem. Soc. 96, 6774 (1974)].

To avoid the difficulties of handling organocuprate compounds i.e. instability above −20° C., sensitivity to oxygen and humidity, other organometallic compounds were studied, i.e. organo zirconium derivatives that are under evaluation for the synthesis of prostaglandins [Organic Synthesis Today and Tomorrow, Ed. by B. M. Trost and C.

R. Hutchinson p. 55, Pergamon Press, Oxford; J.Am. Chem. Soc. 102, 1333 (1980); Tetrahedron Lett 4639 (1976)].

Preparation of the cyclopentenone intermediate

A number of synthetic methods are available for the preparation of hydroxy cyclopentenones (LIII).

The initial work of Yura and Idu led to several syntheses related to prostraglandin analogs [Ann. N.Y. Acad. Sci 180, 64 (1971); J. Med. Chem 26, 786 (1973)].

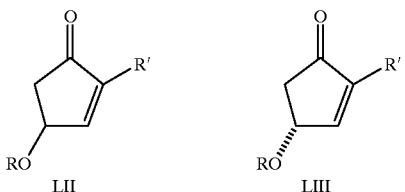

The intermediate LV is synthesized by reacting an appropriate keto acid with dimethyl oxalate. The compound LIV (Scheme 6) is obtained, and then decarboxylated to LV. After reduction and treatment with 1,2-dimethoxypropane in acid methanol, LV is converted to the thermodynamically more stable enol ether LVI. Posterior reduction with Red Al leads to hydroxycyclopentenone LVII [J. Am. Chem. Soc. 97, 865 (1975); Chem. Pharm. Bull. (Tokyo) 25, 1273 (1977); Tetrahedron Lett. 3165 (1976); Tetrahedron Lett. 943 (1973)] (Scheme 6).

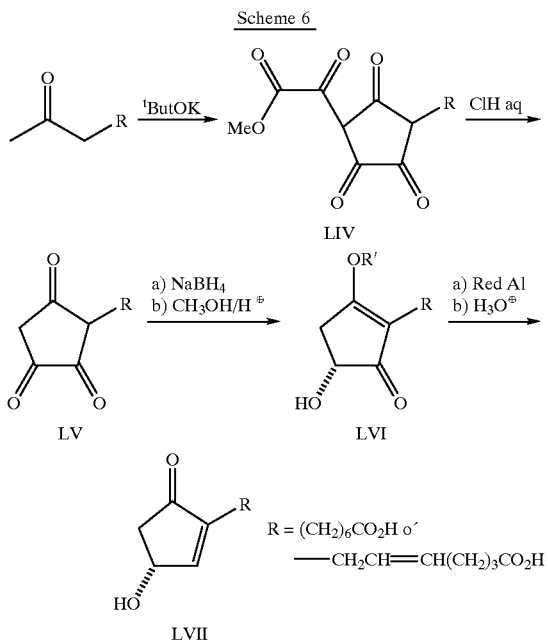

Other synthetic route for the synthesis of hydroxycyclopentenone, starts with furan derivatives; ie: furfural which leads to compound LVIII.

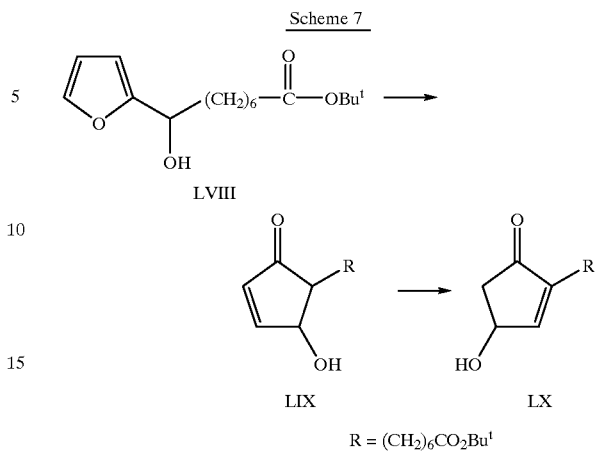

Treatment of LVIII with polyphorphoric acid and isomerization of LIX on alumina gives LX with high yield (Scheme 7). There are other routes for the synthesis of LX i.e: to start from enamine LXI [J. Chem. Soc. (Perkin I), 2550 (1976); Chem. Biochem. and Pharm. Activity of Prostanoids Ed. by S. M. Roberts and Scheinmann 77, Pergamon Press, Oxford, 1979]. This and other methods will not be analyzed here.

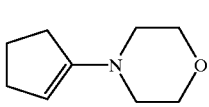

Enolate trapping approach

It is a development of the conjugate addition approach. The α chain is introduced after the conjugate addition by alkylation of the enolate intermediate by an electrophilic reagent. (Scheme 8).

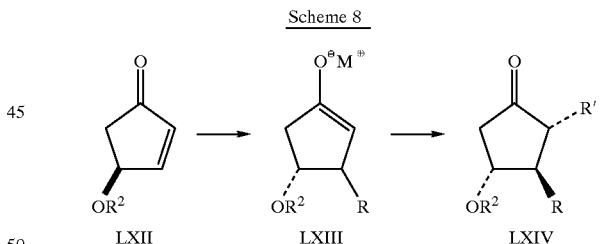

Patterson, Fried and Posner [J. Org. Chem. 39, 2506 (1974); J. Am. Chem. Soc. 97, 107 (1975), Tetrahedron Lett. 2591 (1974)] first applied this approach to the synthesis of 11-deoxy prostaglandins (Scheme 9). The enolate LXVII is alkylated with cis-7-bromo-5-en-heptanoate and 11-deoxy $PGE_2$ was obtained with a global yield of 47%.

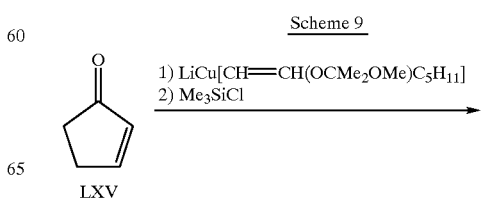

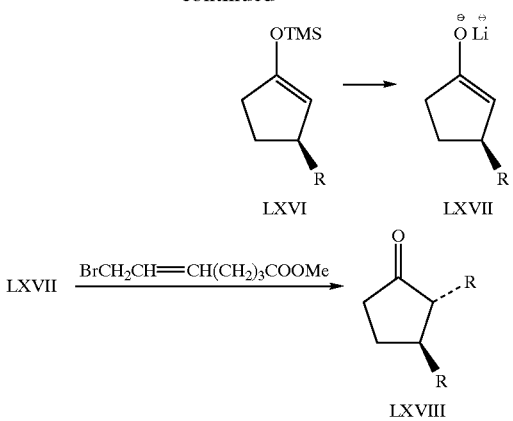

have furnished a variety of useful prostaglandin intermediates [Tetrahedron Lett. 23, 5563 (1982); ibid 4057 (1982)].

Compound LXX is obtained by chiral reduction of LXIX with (S)-BINAL-H (Scheme 10). The silylated enone LXXI underwent conjugate addition by a chiral cuprate, the resulting enolate LXXII is trapped by an aldehyde to give the aldol product. Reduction of $C_1$ hydroxyl function could not be accomplished before preparing intermediate LXXIV to lower the activation reaction energy.

The intermediate LXXV can be converted to $PGE_2$ or $PGE_1$ esters or in $PGF_{1\alpha}$ and $PGF_{2\alpha}$ by well known methods.

Although trapping with alkyl halides or their equivalents has still not been achieved, reaction with more reactive species such as acyl chlorides, aldehydes, Michael acceptors

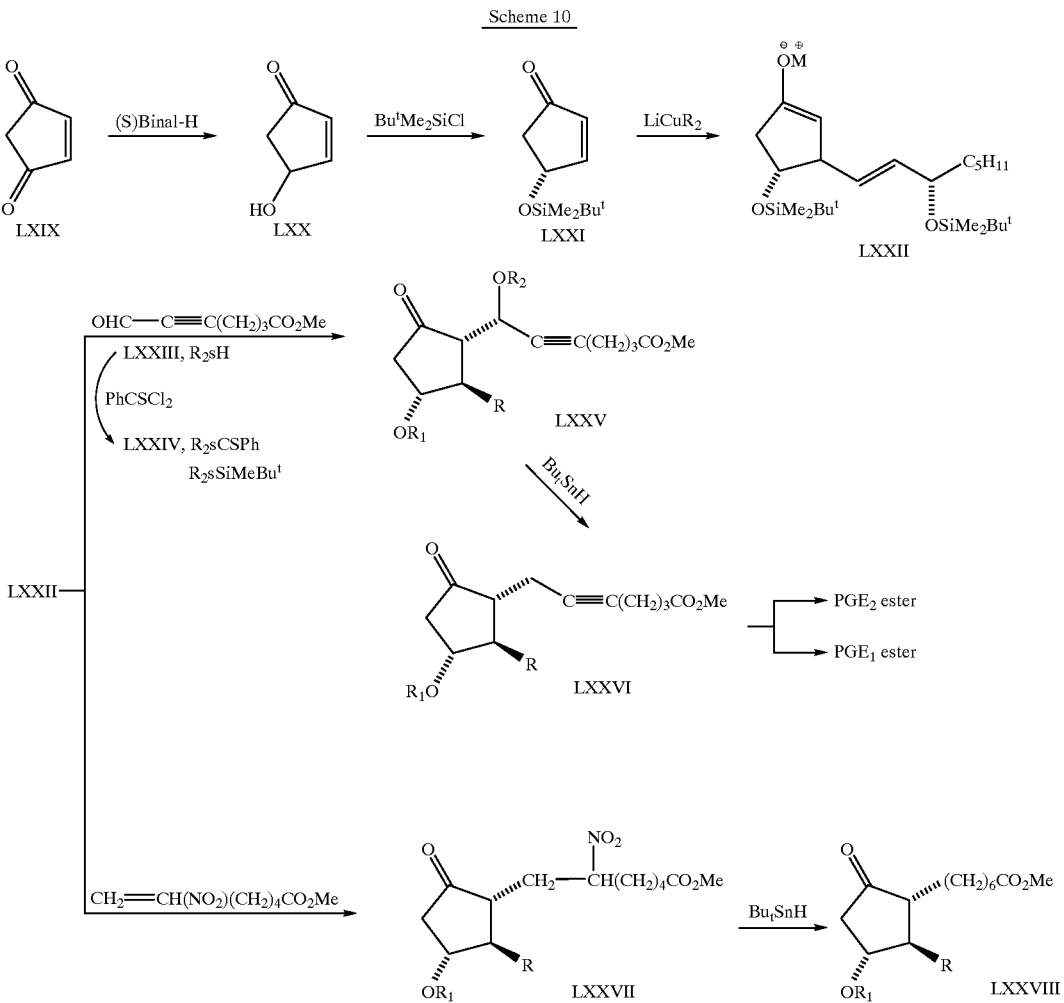

Scheme 10

Proposal (c): Cyclization of Aliphatic precursors

This strategy relates to assemble key functional groups in an aliphatic intermediate which is cyclized to a cyclopentane ring. The synthesis is then completed by conventional methods [Johnson et al. J. Am. Chem. Soc. 104, 2190 (1982)] to obtain PGF$_{2\alpha}$ starting from dimethyl-(S)-4-acetoxy-3,6-dioxosuberate after a long synthesis but with low yield. Other works were performed by Miyano [J. Org. Chem. 40, 1748 (1975)] and Corey [(J. Am. Chem. Soc. 90, 3245 (1968)]. In an example, the cyclopentane ring was formed after a Dieckmann condensation starting from diester LXXIX to obtain PGE$_1$ (Scheme 11). Other groups worked in this approach by clever and elaborated synthetic methods [J. Org. Chem. 38, 4412 (1973); J. Am. Chem. Soc. 90, 3247 (1968); ibid 91, 535 (1969); J. Am. Chem. Soc. 100, 8272 (1978); ibid 98, 1583 (1976); Tetrahedron Lett. 3963 (1973); Bull. Soc. Chim. Fr. 2, 131 (1978)].

Scheme 11

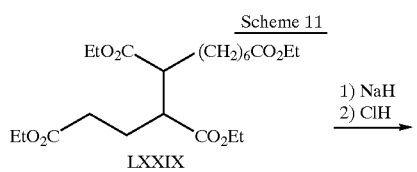

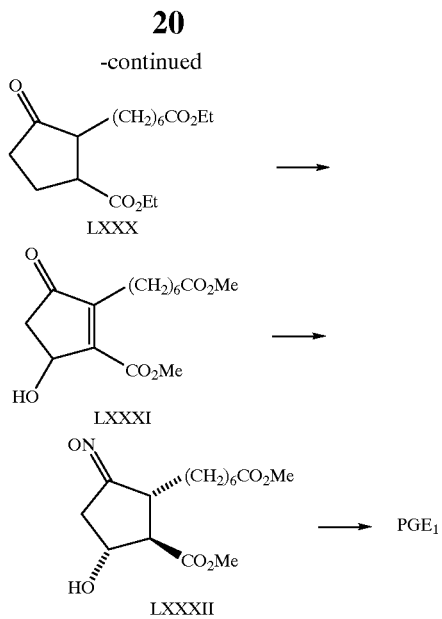

Proposal (d): Prostaglandin Interconversion

It is useful to convert prostaglandins from one series to another. It is mainly applied to the synthesis of analogs. As an example, a synthetic sequence that leads to PGE$_2$ could be used properly modified to obtain PGF$_{2\alpha}$ (scheme 12).

Scheme 12

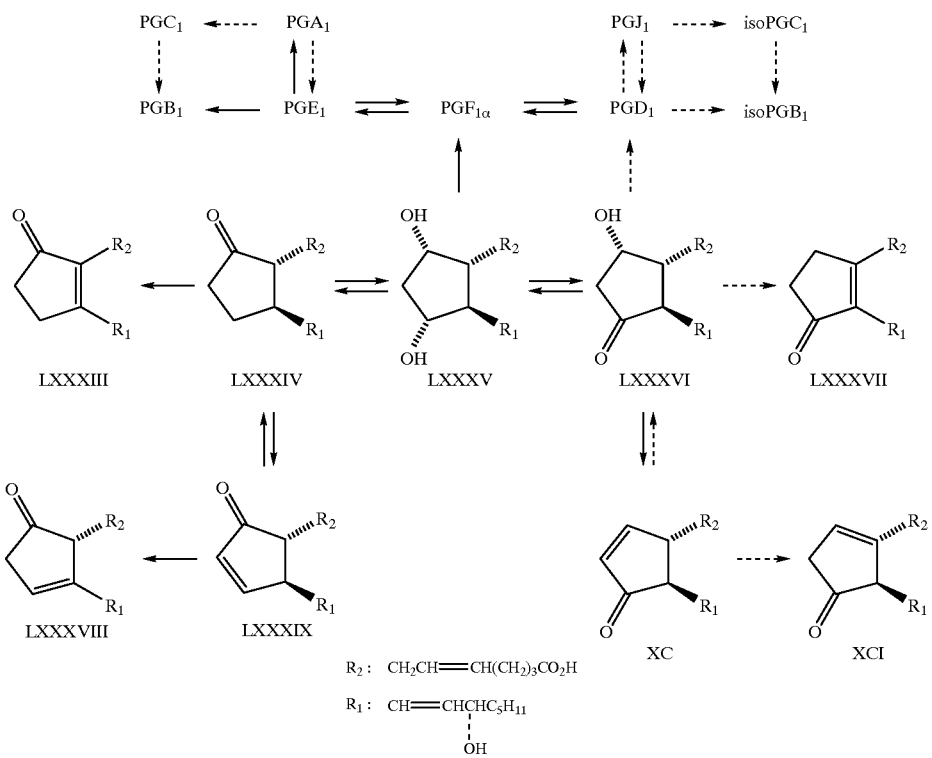

SUMMARY OF THE INVENTION

This invention relates to the discovery of a unique molecule as part of a project for the preparation of series of prostaglandin analogs with a specific uterotonic activity for the induction of labor at term. These molecules are analogs of PGE$_1$ specifically designed for use in the induction of labor at term and have a short duration of action in order to minimize the adverse reactions to mother and fetus.

The molecule backbone could be substituted by different groups leading to different derivatives (Formula I).

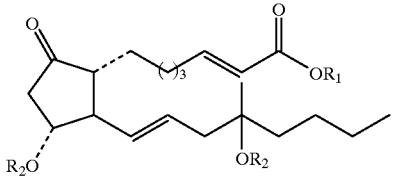

With $R_1$ = H, alkyl or cycloalkyl radical, linear or branched.
$R_2$ = H or silyl derivative or cyclic ether (ie: THP derivative).

The $PGE_1$ analog presented in this invention shows uterotonic properties, enhancing the response to $PGF_2\alpha$ in isolated rat uterus. The drug possesses other pharmacological properties as inhibitor of gastric acid secretion, hypotensive and bronchodilator.

DETAILED DESCRIPTION OF THE INVENTION

The present invention relates to a $PGE_1$ analog, code named B-407, with the structure (CII) and following chemical name: trans-$\Delta^2$-15-deoxy-16-hydroxy-16-methyl $PGE_1$ methyl ester.

B-407, disclosed in this patent, was designed to be pharmacologically active in labor at term. It has been designed considering the structure activity relationship for natural and synthetic prostaglandin analogs taking special care in reducing the adverse effects and improving the safety for both the mother and the baby.

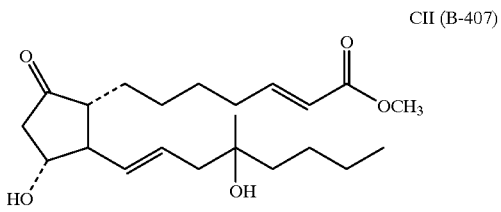

CII (B-407)

For the synthesis of this compound, we have used the conjugate addition approach described in the text. All reactions used have proved to be selective and efficient. The different steps and reaction conditions for the synthesis of B-407 are detailed in schemes 13 to 15.

The conjugate addition approach, in this case, involves the reaction of cyclopentenone XCVI with a lithium organocuprate reagent: and "in situ" capture of the formed enolate by the silylating agent to give XCIX (Scheme 14). The key step in this synthesis, that is the introduction of trans double bond conjugated to the ester group, is achieved by attaching a seleniating agent to the alpha position of the ester group and later oxidation and unprotecting reactions leading to the compound disclosed in this invention (CII, Scheme 14). The enone XCVI was synthesized by the well known cyclopentatrione pathway (Scheme 13) and the lower chain was prepared according to Scheme 15.

All the results presented in the examples are according to our previous plan of synthesis. The reaction of cyclopentadione XCIII with 2,2-dimethoxy propane in acid methanol yields the enol ether XCIV. By a reduction with a metallic hybride and after acid work up, the enone XCV is obtained. This compound is protected by silylating preferably with triethylsilane chloride (Scheme 13).

The protected enone can be treated with a tri-n-butylstannyl XCVIII or an iodine alkenyl derivative CVI to give compound XCIX. The formed enol is trapped as a t-butyl dimethylsylane derivative. In order to obtain the trans $\Delta^2$ double bond, a phenyl selenyl group is introduced in $C_2$ (C), which is oxidatively eliminated by treatment with $H_2O_2$ to yield compound CI. After unprotecting the hydroxyl groups of $C_9$, $C_{11}$ and $C_{19}$ in acidic media, trans $\Delta^2$-15-deoxy-16-hydroxy-16-methyl $PGE_1$ is obtained (CII), named by us as B-407, which is the object of this invention (Scheme 14).

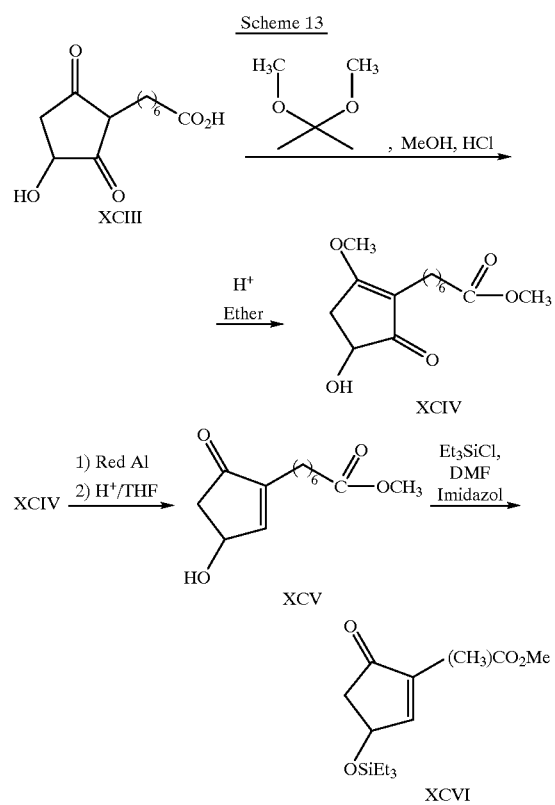

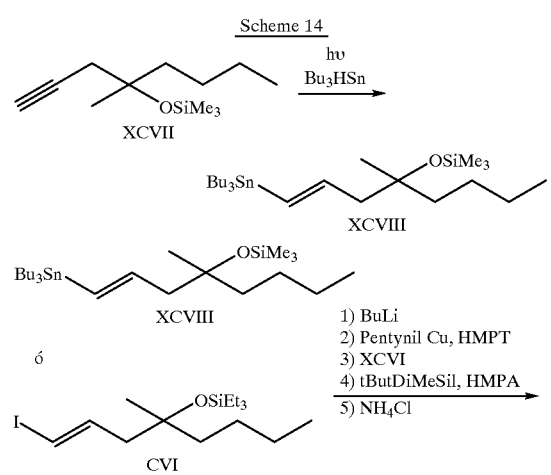

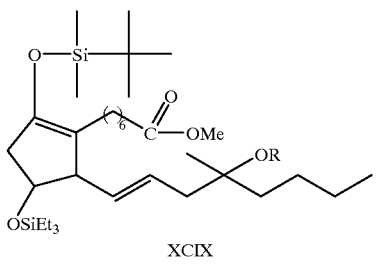
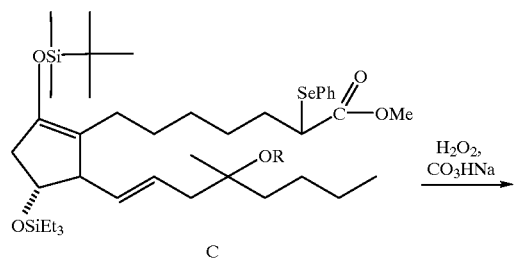
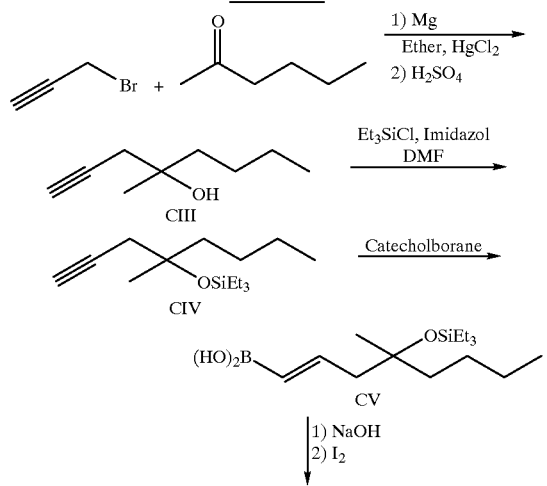
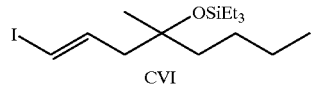

Biological Activity

A series of broad pharmacological studies were carried out to characterize the pharmacology of B-407 both for its primary and secondary characteristics. The studies performed to date indicate that B-407 is a specific uterotonic drug with a good side effect profile. B-407 was specifically designed to be a superior uterotonic drug than existing prostanoids due to the following features inherent in its chemical structure:

a) Improved biological specificity is generally achieved through the transposition of the C-15 hydroxy group to the adjacent 16 Carbon (See Dajani et al.: Prostaglandins 10:733–745, 1975).

b) Increased metabolic inactivation of the upper side that permit decreased duration of effect which is important for limiting potential adverse effects on mother and the baby such as hypertonus.

While the test models used for the pharmacological characterization are not always of a direct nature, those skilled in the art fully recognize the benefits of these models as best predictors of the desired and undesired pharmacological actions in man.

The following pharmacological effects of B-407 both "in vivo" and "in vitro" were determined.

A—Effect on isolated uterus of estrogenized rat.
B—Effect on isolated uterus of rat under diestrous.
C—Effect on the contractility induced by $PGF_{2a}$ on rat isolated uterus.
D—Effect on guinea pig isolated trachea.
E—Effect on the bronchoconstriction induced by histamine aerosol in guinea pig.
F—Effect on arterial blood pressure and heart rate in anaesthetized rat.
G—Diarrheogenic effect in mice.
H—Effect on exploratory activity in mice.
I—Effect on motor activity in mice.
J—Effect on the barbiturate sleeping time in mice.
K—Effect on the volume and acidity of the gastric secretion in dogs.
L—Effect on the disappearance of exogenous $PGF_{2a}$ in rat uterus homogenate.

The studies carried out were consistent with the United States of America "Welfare Act on Use of Laboratory Animals" and "Good Laboratory Practices".

A—Effect of B-407 on Isolated Uterus of Estrogenized Rats

Concentration-response curves were carried out on isolated uterus of estrogenized rats. Female Wistar rats weighing 250 g to 300 g were employed. The animals were pretreated with 0.1 mg/kg of estradiol, subcutaneously, 24 h before the experiment. The whole uterus was dissected and excised and a portion of 1 cm of one horn was incubated in a 10 ml organ bath, at 30° C., bubbled with a mixture of 95% $O_2$ plus 5% $CO_2$. The nutrient solution was De Jalon solution described in the International Pharmacopea $II^{nd}$ Ed. and containing $4 \times 10^{-1}$M sodium diclofenac. The organ was left to stabilize in the solution for one hour. No spontaneous contractions were detected under these experimental conditions. To carry out the concentration-response curves, volumes of solutions of either natural prostaglandins or B-407 were added in order to obtain concentrations in the organ bath between $10^{-10}$M and $3\times10^{-6}$M. After 2 minutes, the organ was washed three times during a 15 minutes time period before adding the next test solution. In this way the concentration-response curves obtained were not cumulative ["The rat uterus preparation" in "Pharmacological Experiments on Isolated Preparations". E. and S. Livingstone Ltd. Edinburgh and London (1968), p. 92].

Recording of the contractions of the isolated uterus were on a Berger polygraph with a FT03C transducer. The frequency and magnitude of the responses were globally evaluated by calculating the total area recorded at fixed time periods as will be further explained.

| | Area (g of tension/2 min) | | | | | |
|---|---|---|---|---|---|---|
| Molar Conc. | $1 \times 10^{-10}$ | $1 \times 10^{-9}$ | $1 \times 10^{-8}$ | $1 \times 10^{-7}$ | $1 \times 10^{-6}$ | $3 \times 10^{-6}$ |
| $\overline{X}$ | 0.14 | 0.12 | 0.20 | 0.31 | 1.13 | 0.67 |
| S. E. | 0.10 | 0.08 | 0.17 | 0.19 | 0.58 | 0.39 |
| n | 6 | 6 | 6 | 6 | 6 | 5 |

$\overline{X}$ = Average; S.E. = Standard Error

B-407 exhibited a low effect on rat uterine contractility "in vitro". It is about 4 times less potent than that of $PGE_1$ (Results are not shown).

B—Effect of B-407 on Isolated Uterus of Diestrous Rat ($B_1$)—Concentration-response curves on isolated rat uterus under diestrous condition were carried out. Wistar rats weighing 250 g to 300 g were employed. The diestrous phase was detected by a daily vaginal smear. The uterus was dissected out and a portion of a horn was placed in a 10 ml organ bath in a similar way to that described in part A. The bath temperature was maintained at 37° C., bubbled with a mixture of 95% $O_2$ and 5% $CO_2$ in a Krebs nutrient solution. The organ was left to stabilize for one hour. The isolated uterus presented basal spontaneous contractions under these experimental conditions. Cumulative concentration-response curves were carried out with the addition of either 100 μl or 300 μl of solutions of either natural prostaglandins or B-407 in concentrations of $10^{-10}$M to $10^{-6}$M, each 15 minutes without any washing. Uterine contractions and quantitation were performed as described in (A).

($B_2$)—Concentration-response curves in isolated uterus under diestrous (without any spontaneous contractions) were carried out. Sodium diclofenac was added to De Jalon nutrient solution to a final concentration of $4\times10^{-6}$M. The organ was left to stabilize until the absence of spontaneous contractions. Non-cumulative concentration-response curves were obtained. Recordings of the contractions and their quantitation were performed as described in (A).

| Molar Concentration | Area (g of tension/2 min) | | | | |
|---|---|---|---|---|---|
| | Basal | $1 \times 10^{-9}$ | $1 \times 10^{-8}$ | $1 \times 10^{-7}$ | $1 \times 10^{-6}$ |
| $B_1$ | | | | | |
| $\overline{X}$ (average) | 5.85 | 6.14 | 6.88 | 7.38 | 6.46 |
| Std. Error | 1.53 | 1.51 | 2.00 | 2.13 | 1.55 |
| n | 6 | 6 | 6 | 6 | 6 |
| $B^2$ | | | | | |
| $\overline{X}$ | 1.96 | 1.91 | 2.10 | 3.73 | 4.24 |
| Std. Error | 0.42 | 0.33 | 0.17 | 0.48 | 0.66 |
| n | 6 | 6 | 6 | 6 | 6 |

The basal spontaneous contractions observed in isolated uterus of rats under diestrous were diminished by diclofenac ($B_2$). In this case, a dose-response uterotonic effect of B-407 was observed with a maximum response which duplicates the basal one.

C—Effect of B-407 on the $PGF_{2a}$ Induced In Vitro Contraction of Rat Uterus ($C_1$) Rat Uterus Under Estrous Condition The experimental conditions were identical to those described in part A for the concentration-response curves without spontaneous contractions.

The uterus was allowed to equilibrate in a $10^{-8}$M $PGF_{2a}$ solution for 2 minutes, then the uterus was washed again during 15 minutes. This whole treatment was repeated twice.

Then, a known concentration of the test prostaglandin was added and no washed was carried out during the following 15 minutes. $PGF_{2a}$ ($10^{-8}$M) was added, washing once after 2 minutes and then twice over a total time period of 15 minutes. The result was expressed as the relationship between the effect of $PGF_{2a}$ after the treatment with B-407 and the sum of the effect of $PGF_{2a}$ (mean of the three initial additions) and the effect of B-407 "per se". The recordings of the contractions and their quantitation were performed as described in (A).

| | Nut. | B-407 [M] | | |
|---|---|---|---|---|
| $PGF_{2a}$+ | Sol. | $3 \times 10^{-9}$ | $3 \times 10^{-8}$ | $1 \times 10^{-7}$ |
| Ratio | 0.84 | 1.29 | 1.69 | 2.06 |
| S. E. | 0.06 | 0.05 | 0.25 | 0.22 |
| n | 12 | 6 | 8 | 6* |

($C_2$) Rat Uterus Under Diestrous Condition

The experimental conditions were identical to those described in $B_2$ and the working protocol was similar to that of $C_1$ but the $PGF_{2a}$ concentration was of $10^{-9}$M. The recordings of the contractions and their quantitation were performed as described in (A).

| | Nut. | B-407 [M] |
|---|---|---|
| $PGF_{2a}$ + | Sol. | ($3 \times 10^{-8}$ M) |
| Ratio | 1.04 | 2.35 |
| S. E. | 0.08 | 0.43 |
| n | 6 | 7** |

*p < 0.05: Tested vs. nutrient solution by ANOVA and Schaffe.
* *p < 0.02: Tested vs. nutrient solution by Student's-t-test.
Ratio = Effect of $PGF_{2a}$ after B-407/(Effect of PG $F_{2a}$ before B-407 + Effect of B-407).
S. E. = Standard Error Priming the isolated rat uterus (under both estrous and diestrous conditions) with B-407 significantly potentiated the contractile response induced by $PGF_{2a}$.

Quantitation of areas of (A), (B) and (C):

The frequency and magnitude of the responses were globally evaluated by calculating the total area recorded at a fixed time period as will be further explained. The areas under the curve of the recording paper, over 15 minutes periods, were cut and weighed both in the concentration-response curves and in the potentiating experiments.

The calibration was made by weighing a piece of paper which corresponded to a tension of 1 g at the working sensitivity along 2 minutes. Therefore, a relationship of area expressed in g/2 min was obtained and then the weight of the areas of the responses were transformed to unities of area. The results were expressed as the mean ± the standard error of the areas obtained. The statistical evaluation of the differences was carried out either by ANOVA or by Student's-t-test, as appropriate.

D—Effect of B-407 on "In Vitro" Guinea Pig Trachea

The effect of B-407 on isolated trachea was evaluated in guinea pigs weighing 700 g. The animals were killed and the trachea was dissected out, transferred to a dish containing Krebs solution and cut transversely between the segments of cartilage, so as to give a number of rings of tracheal muscle. Five rings were tied up together with cotton threads, so as to form a chain, which was then mounted in a 10 ml bath with Krebs solution at 37° C., aerated with a mixture of oxygen (95%) and carbon dioxide (5%). The load on the lever was 0.4 g. The organ was left to stabilize for 15 to 30 min.

Enough quantity (100 µl) of 0.1 mM histamine solution was added to the bath ($1 \times 10^{-6}$M) in order to obtain a contraction of 0.2 g to 0.5 g of tension. After the contraction reached a plateau, 100 µl of ethanol:distilled water (1:1) (vehicle as control) was added to the bath. Eight minutes later, the preparation was relaxed by washing 4 to 6 times. Then, the working protocol was repeated, but this time, when the contraction reached a plateau, 100 µl of 1 mM B-407 solution (bath concentrations $1 \times 10^{-5}$M) was added and allowed to act until the relaxation plateau was obtained (no more than 8 minutes).

The relaxation induced by B-407 was expressed as a percentage on the histamine induced contraction. The average ± standard error of all the determinations were calculated ["The guinea-pig tracheal chain"; "Pharmacological Experiments on Isolated Preparations". E. and S. Livingstone Ltd. Edinburgh and London (1968), p. 100; Brit. J. Pharmacol. 22, 511 (1964)].

| Treatment | % of relaxation (n = 8) |
|---|---|
| Vehicle | −7 ± 3 |
| B-407 [$10^{-5}$ M] | 35 ± 5 |

B-407 induced relaxation of histamine contracted guinea-pig tracheal chains.

E—Effect of B-407 on the Guinea Pig Histamine-Aerosol Induced Bronchoconstriction The protective effect of B-407 on the bronchoconstriction induced by histamine aerosol in male guinea pigs weighting 700 g was evaluated. One guinea pig at a time was placed into a 15 l hermetically closed container. Then 200 µl of histamine solution (600 µg of histamine base) was sprayed with compressed air at a pressure of 1 PSI. The time at which the hypoxic symptoms (increase of breathing frequency, bronchospasm, dysnea, apnea and finally the collapse of the animal (falling down) was determined.

The working protocol comprised 3 parts:
1) The determination of the falling down time of the guinea pigs exposed to the histamine aerosol was determined. The animal was considered to exhibit positive response for the assay if it fell down before 150 seconds.
2) Three days later, the guinea-pigs were tested with a dose of 150 µg/kg of B-407, administered intraperitoneally (0.2 ml/100 g), 5 minutes before the histamine challenge.
3) Three days later, the part 1 of the assay was repeated again.

The results were expressed as the time in seconds elapsed before the animals fell down ["Antihistamine Agents" (Cap. 22) in: "Screening Methods in Pharmacology", Academic Press, New York (1965). Brit. J. Pharmacology, 16, 59 (1961); Arch. Intern. Pharmacodyn. 129, 77 (1960); J. Pharmacol. Exptl. Therap. 131, 73 (1961); Arch. Intern. Pharmacodyn. 115, 332 (1958); "Les Antihistaminiques de Synthése", Chapter 22, page 784 in: "Structure of activité pharmacodynamique de médicaments due systéme nerveux vegetatif". S. Karger Bale (Suisse)—New York. (1948)].

| Falling down time (sec) by bronchospasm (n = 8) | | |
|---|---|---|
| Initial (72 h before) | B-407 (150 µg/kg, i. p.) | Final (72 h after) |
| 115 ± 8 | 358 ± 4 | 127 ± 4 |

B-407 showed a protective effect on the guinea-pig histamine induced bronchoconstriction.

F—Effect of B-407 on Blood Pressure and Heart Rate in Anesthetized Rat

The acute effect of B-407 on the cardiovascular system was studied. After doses of 10 µg/kg, 30 µg/kg, and 100 µg/kg, administered intravenously (i.v.) the arterial blood pressure and heart rate were evaluated on male Wistar rats weighing 300 g to 350 g. Rats were anesthetized with 40 mg/kg, i.p., of sodium pentobarbital. The left jugular vein was cannulated by means of polyethylene tubing to allow the i.v. administration of drugs. The trachea was cannulated to facilitate ventilation and the right carotid artery was cannulated to record blood pressure and heart beat. A dose of 350 UI/kg, i.v., sodium heparin was administered. The catheter of the artery was connected to a pressure transducer attached to a Berger polygraph. The volume of the i.v. administrations was 0.4 ml/kg. The working protocol was as follows:

A steady-state recording was obtained over a 30 minutes time period. Then a dose of 0.5 µg/kg of noradrenaline followed by 0.5 µg/kg of isoproterenol were administered over 5 to 10 minutes. After 5 min of recording, increasing doses of B-407 were administered every 15 minutes. The mean arterial blood pressure (mm Hg) was obtained by calculating the average of the values of systolic blood pressure. The heart rate (beats/min) was obtained by counting the number of contractions by units of time.

| Treatment (n = 6) | ΔMBP (mm Hg) | Higher lasting time (min) | HR (Beats/min) |
|---|---|---|---|
| B-407 (µg/kg, i. v.) | | | |
| 10 | −11.0 ± 1.3 | 0.66 | 430.6 ± 7.2 |
| 30 | −29.8 ± 3.8 | 2.5 | 420.7 ± 4.1 |
| 100 | −47.7 ± 3.3 | 5.5 | 452.7 ± 16.7 |
| Basal | 120.9 ± 4.6 (MBP) | | 440.8 ± 9.7 |

B-407, administered in a single i.v. injection, showed a transient dose-dependent hypotensive action and a slight increase of the heart rate in the anesthetized rat.

G—Diarrheagenic Effect of B-407 on Mice

The diarrheagenic effect of the synthetic $PGE_1$ analog B-407 was evaluated in Swiss mice. The effect of the intraperitoneal and intravaginal routes of administration were studied as follows:

a) Intraperitonial administration:

Six groups of ten mice (25 to 30 g) each (5 ♂ and 5 ♀) were used. They received i.p. doses of 0; 1; 3; 10; 30 and 100 μg/kg of the test drug. The diarrheagenic response was evaluated on an "all-or-none" basis as described in section C.

b) Intravaginal administration (i.vag.):

A seven points dose-response curve was performed for B-407. Eight groups of six mice (18 to 25 g) each received doses of 0; 10; 18; 32; 56; 100; 160 and 250 μg/kg of B-407.

The intravaginal administration was made through a polyethylene catheter attached to a 1 ml syringe. This system allows the delivery of volumes of 10 to 15 μl.

The animals were evaluated in an "all-or-none" basis as the ratio of the number of animals with diarrhea over the total number of mice in the group. The median effective doses (ED50) with their fiducial limits and the statistics were performed according Litchfield and Wilcoxon [Eur. J. Pharmacol. 34, 105 (1975); J. Pharmacol. Exp. Ther., 95, 99 (1949)].

| Route | i. p. | i. vag. |
| --- | --- | --- |
| ED50 (μg/kg) | 4.12 | 58.3 |
| SCL | 8.65 | 124.9 |
| ICL | 1.95 | 27.4 |
| n | 10 | 6 | i. p. = Intraperitoneal
i. vag. = Intravaginal
SCL = Superior confidence limit
ICL = Inferior confidence limit B-407, both i.p. and i.vag., induced dose-dependent diarrheagenic effects. However, the i.vag. route showed a desirable lower potency since this is the preferred route of administration in obstetrics.

H—Effect of B-407 on Exploratory Activity on Mice

The effect of B-407 on the exploratory activity was evaluated in Swiss mice of 30 g to 40 g in an open-field of 40 cm×40 cm×25 cm divided in 9 quadrants. One mouse at a time was placed into the open field to assess its exploratory activity by counting the number of quadrants crossed in 4 consecutive periods of 3 minutes each.

The working protocol consisted of two experiments with 3 groups of 10 animals each. In both experiments, each group of mice were pretreated with B-407, 0 μg/kg, 30 μg/kg and 100 μg/kg five min prior to the test. In one experiment, the animals were treated, p.o., with a combination of the antispasmodics homatropine methylbromide (5 mg/kg) and papaverine (5 mg/kg) administered 10 min prior to B-407. In the other experiment, this treatment was replaced by saline solution. The two experiments were carried out at the same time.

The results were expressed as the average ± standard error of each group and the statistical significance of the differences were evaluated by means of the Student's-t-test.

| Dose (μg/kg, i. p.) | N Quadrants/12 min (n = 10) |
| --- | --- |
| 0 | 88 ± 8 |
| 30 | 87 ± 8 |
| 100 | 48 ± 8* |

*$p < 0.05$: Student's-t-test vs. control group

B-407 produced a significant decrease in the exploratory activity in mice.

I—Effect of B-407 on Motor Activity in Mice

The effect of B-407 on motor activity was evaluated in fasted Swiss male mice of 18 g to 24 g. The motor co-ordination activity in mice was determined by placing the animals on a rota-rod, rotating cylinder at a speed of 7 r.p.m. and determining if the animal could remain on the rota-rod for at least 5 minutes.

Three groups of 10 animals each received the following treatments 15 min prior to the test:

1) Distilled water (0.1 ml/10 g, i.p.).
2) B-407 100 μg/kg (0.1 ml/10 g, i.p.).
3) Diazepam 5 mg/kg (0.05 ml/10 g, p.o.).

Group 3 constituted as a positive control of the method.

The motor activity was evaluated on an "all-or-none" basis. The results were expressed as the ratio of the number of animals which remained on the rota-rod less than 5 minutes/total number of animals assayed for each group [J. Am. Pharm. Assoc. 46 (3), 208 (1957)].

| Treatment (n = 10) | Fraction |
| --- | --- |
| Vehicle | 0/10 |
| B-407 (100 μg/kg, i. p.) | 1/10 |
| Diazepam (5 μg/kg, i. p.) | 8/10 |

Fraction equals to the animals fallen before 300 sec/total number of animals.

After the administration of B-407, no significant effect on the motor co-ordination activity was observed in mice.

J—Effect of B-407 on the Barbiturate Sleeping Time in Mice

The effect of B-407 on the time of induction and time of duration of the barbiturate sleeping time was evaluated by determining the time of loss and recovery of the righting reflex. This was carried out in Swiss female mice weighing 20 g to 25 g.

Two groups of 12 mice each were used. One group was treated with B-407 (100 μg/kg, i.p.). Fifteen minutes later, pentobarbital sodium ]30 mg/kg, i.p.) was administered. The time of onset (the loss of the righting reflex) and of duration (the elapsed time from the loss of the righting reflex up to its recovery from the barbiturate-induced sleeping) were determined. Full recovery of the righting reflex was assumed when the animal, placed on its back, could recover its normal position at least 3 times during one minute. The control mice group followed the same protocol, but received saline solution instead B-407. The results were expressed as the average ± standard error of each group and the statistical significance of the differences were evaluated by means of the Student's-t-test.

| Induction time (min) | | Sleeping time (min) | |
|---|---|---|---|
| Control | B-407 (100 μg/kg, ip) | Control | B-407 (100 μg/kg, ip) |
| 4.52 ± 0.22 | 3.75 ± 0.19 | 27.8 ± 3.10 | 29.7 ± 2.91 |
| | $p < 0.02$ | | n. s. |
| | n = 12 | | n = 12 | n.s. = non significant

B-407 provoked a slight but significant decrease in the time of onset of the barbiturate-induced sleeping time without affecting its duration.

K—Effect of on the Volume and Acidity of Gastric Secretion in Dogs

Healthy adult Beagle dogs weighing 10 kg to 13 kg were used.

The basal response of each dog to histamine, as represented by volume of gastric secretion and acid concentration, was carried out six times. For this purpose the dogs were placed in a Pavlov support and plastic bottles were connected to a Thomas type gastric fistula after cleaning it when necessary.

Saline i.v. infusion was started by means of a Butterfly G 21 (Abbot) needle connected to a 500 ml bottle of sterile pyrogen free isotonic saline solution through an inert plastic cannula. The solution dripping was adjusted to 1 ml/min.

The volume of gastric secretion obtained from fifteen minutes collection periods, expressed as ml/15 min, was determined. Aliquots of 5 ml were kept in the freezer to perform acid titration on the next day. The first three collection periods were considered as the actual basal gastric secretion for each dog in the absence of any drug. Then the bottle of saline was changed for a solution of histamine, 2 HCl at a concentration of 16.4 μl/ml in saline. The dripping was adjusted 20 drops per minute (984 μg histamine/hour). After the plateau of augmented gastric secretion was reached, B-407 was administered.

Acid concentration, expressed as mEq H+/1 was determined by titration with sodium hydroxide.

L—Effect of B-407 on the Disappearance of Exogenous $PGF_{2\alpha}$ in Rat Uterus Homogenate An experiment was performed in which the disappearance of exogenous $PGF_{2\alpha}$ was determined in the nutrient solution of slices of rat uterus both in the presence and absence of the synthetic $PGE_1$ analog, B-407.

Seven Wistar rats weighing approximately 220 g were estrogenized by the subcutaneous administration of 100 μg/kg of 17-β-estradiol. Twenty-four hours later they were killed by decapitation. The uterine horns were dissected out and weighed. The horns were cut and washed with bubbled De Jalon nutrient solution plus $4\times10^{-1}M$ sodium diclofenac during 15 to 20 minutes. Both bubbling and diclofenac content were maintained in the following steps: each horn was then placed in a small organ bath and preincubated during 15 to 20 min with either the nutrient solution alone or containing B-407 $10^{-8}M$ or $10^{-7}M$. The assay was started by adding exogenous $PGF_{2\alpha}$ ($10^{-8}M$ in the medium) to each horn previously changed to a new tube. A final volume of 0.4 ml was obtained with the addition of De Jalon solution at 37° C. Aliquots of 200 μl were sampled at 0 min, 5 min, 15 min and 30 min. The $PGF_{2\alpha}$ concentration in each sample was determined by R.I.A. (Sigma, NEN) and it was expressed as pg/mg of wet tissue.

| | $PGF_{2\alpha}$ (pg/mg tissue) | | |
|---|---|---|---|
| Time | | B-407 [M] | |
| (min) | Control | $10^{-8}$ | $10^{-7}$ |
| 0 | 655.4 | 705.7 | 667.2 |
| 5 | 582.8 | 705.9 | 623.7 |
| 15 | 478.4 | 563.6 | 561.7 |
| 30 | 227.5 | 403.7 | 528.4 |

A concentration-dependent inhibition of the disappearance of exogenous $PGF_{2\alpha}$ by B-407 was found, after 30 minutes of incubation, in rat uterine slices.

It is concluded that B-407 has useful and specific uterotonic activity. The drug also has bronchodilating, hypotensive and gastric antisecretory activity.

| | | VOLUME (ml/15 min) | | | ACIDITY (mEg.H⁴/l) | | |
|---|---|---|---|---|---|---|---|
| Route (n = 6) | Dose (μg/kg) | Histadine Plateau | Max. eff. B-407 | % Inhib. | Histamine Plateau | Max. Eff. B-407 | % Inhib |
| i. v. | 1 | 39.5 ± 3.4 | 33.5 ± 3.6 | 15.2 | 133.6 ± 7.5 | — | — |
| i. v. | 3* | 43.2 ± 4.6 | 2.7 ± 1.3 | 93.7 | 145.3 ± 3.0 | 58.5 ± 16.0 | 59.7 |
| i. g. | 10 | 42.0 ± 3.6 | 31.8 ± 6.2 | 24.3 | 122.4 ± 9.7 | 70.4 ± 11.8 | 42.5 |
| i. g. | 30** | 38.3 ± 2.6 | 24.4 ± 3.1 | 36.3 | 143.4 ± 3.2 | 97.8 ± 13.2 | 31.8 |
| i. vag. | 1 | 50.8 ± 2.4 | 35.3 ± 5.3 | 30.5 | 134.2 ± 6.4 | 101.4 ± 13.3 | 24.4 |
| i. vag. | 3 | 49.1 ± 2.5 | 0.8 ± 0.4 | 98.4 | 132.6 ± 8.7 | 37.8 ± 12.1 | 71.5 |
| i. vag | 10 (n = 3) | 43.0 ± 2.0 | 0.0 | 100.0 | 141.5 ± 4.3 | — | — |
| i. vag | 30 (n = 2) | 38.5 ± 8.5 | 2.4 ± 1.7 | 93.8 | 118.9 ± 4.3 | 38.9 ± 19.9 | 67.3 |

*Retching and trembling
**Retching and trembling
Plateau = Volume or acidity corresponding to the secretory maximal effect of histamine.
Max. Eff. = Volume or acidity corresponding to the maximal inhibitory effect of B-407.

The percentages of inhibition obtained pointed out that the i.v. and i.vag. routes would be considered bioequivalent whereas the i.g. route would require the administration of doses 1 to 1.5 log units higher in order to obtain similar effects to the other routes.

Organic Synthesis

EXAMPLE 1

A solution of 15.02 g of dimethyl malonate in 50 ml of MeOH was cooled to 15° C. and treated dropwise over a 2 h period with a solution of 2.4 g of LiOH in 20 ml of water.

The mixture was stirred for 30 min after the addition was completed and then stripped of solvent under reduced pressure. The residue was taken up in 100 ml of hot MeOH, the solution cooled to room temperature and filtered. The filtrate was stripped of solvent to dryness. The residue was suspended in 100 ml of toluene and stripped further to remove the remaining water. The solution was cooled to room temperature and the precipitate collected by filtration to give 9.66 g (68%) of lithium mono methyl malonate. IR cm$^{-1}$): 1730, 1605, 1580.

EXAMPLE 2

Imidazole (6.37 g) was dissolved in 40 ml of THF and a solution of 2.78 g of thionyl chloride in 10 ml of THF was added dropwise with stirring and cooling (T<15° C.). The mixture was allowed to stir for 1.5 h at room temperature and then filtered under nitrogen in a filtering chamber. The white precipitate was washed with 10 ml of THF and the filtered solution was treated with 4.73 g of monomethyl azelaic acid. The resulting solution was stirred at room temperature for one hour.

In other flask, 3 g of lithium monomethyl malonate was suspended in a mixture of 7.5 ml of HMPA and 20 ml of THF and treated with cooling with 7.8 ml of methylmagnesium bromide 3M in ether keeping the temperature below 10° C. After the addition ended the solution was stirred at room temperature for 30 min. The imidazole solution described above was added, keeping the temperature below 20° C. and the mixture was stirred overnight at room temperature and poured into a mixture of ice/water and 5 ml of HCl (c). The mixture was extracted 3×20 m l of benzene and the organic layer washed (brine, 5% $Na_2CO_3$, brine), dried over $Na_2SO_4$ (anhydrous) and stripped of solvent under reduced pressure. Distillation "in vacuo" gave 2.7 g (43%) of a yellow oil. IR (cm$^{-1}$): 1730, 1710; bp: 135–7° C. (0.3 mm Hg).

EXAMPLE 3

To a solution of 1.55 g of dimethyl 3-ketoundecadioate in 4.5 ml of MeOH, 0.85 g of NaOH in 4.5 ml of water was added with cooling and the mixture allowed to stand at room temperature overnight. The solution was heated on a silicone bath at 100° C. for 30 min, cooled, extracted 2×10 ml with ether:benzene (1:1), acidified with 2N HCl and placed in the silicone bat at 100° C. for 30 min. The mixture was cooled and extracted with ether:benzene (1:1). The organic layer was dried over anhydrous $Na_2SO_4$ and stripped of solvent under reduced pressure and the residue was recrystallized from hexane:ether (2:1) to give 0.99 g (88%) of product. IR (cm$^{-1}$): 1700; mp: 43–5° C.

EXAMPLE 4

To a mechanically stirred refluxing solution of 1.61 g potassium metal in 28 ml of t-BuOH, a solution of 1.55 g of 9-oxodecanoic acid and 2.82 g of dimethyl oxalate in 15 ml of t-BuOH was added dropwise. After the addition was complete, refluxing was continued for 2 h. The reaction mixture was cooled and filtered under nitrogen. The filtered cake was washed with 1N HCl and the resulting mixture extracted with chloroform. The organic layer was washed with water, dried over anhydrous $Na_2SO_4$ and stripped of solvent under reduced pressure to give 2.53 g (87%) of a yellow oil that was used without any further purification.

EXAMPLE 5

A mixture of 27.85 g of 2,3,5-trioxo-4-methoxalylcyclopentaneheptanoic acid and 700 ml of 1N HCl was refluxed under nitrogen for 2 h, cooled and the suspension was extracted with EtAcO (4×150 ml), the organic layer washed with water, dried ($Na_2SO_4$, anhydrous) and stripped of solvent to yield 19.71 g of a yellow oil that was chromatographed using silica gel and hexane:EtAcO:AcOH 60:60:1 as eluent to yield 13.31 g (69%) of a yellow solid. IR (cm$^{-1}$): 1740, 1690, 1670, 1380; mp: 102–3° C.

EXAMPLE 6

To a solution of 1.92 g of 2,3,5-trioxocyclopentanheptanoic acid in a mixture of 62 ml of EtOH and 76 ml of water, 1.1 g of solid $NaBH_4$ was added, at 0–5° C. The solution was stirred for 30 min at this temperature and quenched with 1N HCl. The solution was stripped of EtOH at room temperature and reduced pressure, and the resulting solution extracted with EtAcO (3×50 ml). The extracts were combined, washed (brine:water 1:1), dried over anhydrous $Na_2SO_4$ and evaporated to dryness under reduced pressure to give 1.91 g (98%) of product. IR (cm$^{-1}$): 3400, 1700, 1560, 1380; mp: 124–6° C.

EXAMPLE 7

To a solution of 350 mg of 2,5-dioxo-3-hydroxycyclopentane heptanoic acid (XCIII) in 7 ml of MeOH, 2 ml of 2,2-dimethoxypropane and 0.8 ml of 1% methanolic HCl were added. The mixture was allowed to stand at room temperature 48 h and then it was stripped to dryness at room temperature and under reduced pressure. About 1 ml of ether was added and the mixture was allowed to stand at room temperature for 48 h. The solidified mixture was taken up in benzene containing 1% triethylamine and the solution was washed successively with dilute $K_2CO_3$, saturated $NH_4Cl$ and brine, dried over anhydrous $Na_2SO_4$ and stripped of solvent under reduced pressure. The residue crystallized upon addition of ether to give 124 mg (32%) of XCIV as a white solid (Scheme 13). IR (cm$^{-1}$): 3400, 1765, 1730, 1685, 1670; mp: 88° C.

EXAMPLE 8

Dry toluene (10 ml) was placed in a flask and cooled to −70° C. In separate dropping funnels, 0.55 ml of 3.4M Red Al diluted with 7.5 ml of toluene and a solution of 0.460 g of methyl-7-(4-hydroxy-2-methoxy-5-oxocyclopent-1-ene) heptanoate in 25 ml of toluene were placed. The two solutions were added dropwise and simultaneously to the flask over a 15 min period. The temperature of the reaction mixture was not allowed to exceed −60° C. during the additions. The mixture was stirred at −70° C. for 3.5 h and at 0° C. for 15 min, quenched with MeOH and acidified with 1N HCl. The organic layer was separated, washed successively with diluted $NaHCO_3$ and water, dried over anhydrous $Na_2SO_4$ and stripped of solvent under reduced pressure. The residue was dissolved in 11 ml of THF and 1.5 ml of 1N HCl and placed in the refrigerator overnight. The THF was evaporated and the residue diluted with EtAcO. The organic layer was separated and washed successively with 1% $NaHCO_3$ and water, dried over anhydrous $Na_2SO_4$ and stripped of solvent under reduced pressure. The residue was crystallized from ether to give 110 mg (27%) of XCV as a white solid. mp:45–6° C. IR (cm$^{-1}$): 3400, 3050, 1730, 1680, 1630.

EXAMPLE 9

A solution of 100 mg of methyl-7-(3-hydroxy-5-oxocyclopent-1-ene) heptanoate XCV in 0.7 ml of DMF was treated with 46 mg of imidazole and 78 mg of triethylchlorosilane and stirred at room temperature for 90 min. The mixture was poured over 25 ml of ice water and extracted with ether. The ether extracts were combined and washed with brine, dried over anhydrous $Na_2SO_4$ and evaporated. The residue was chromatographed (silica gel/hexane:EtAcO; 95:5) to yield 132.2 mg (90%) of product (XCVI). I.R. ($cm^{-1}$): 1730, 1710, 1080, 740.

EXAMPLE 10

A mixture of 4 g of 4-trimethylsilyloxy-4-methyl-1-octyne (XCVII) and 4.22 ml of recently distilled $HSnBu_3$ was heated under $N_2$ at approximately 50–60° C. using a sunlamp of 150 W placed at a distance of 10 cm for 5 h. The triethylsilyl derivative could be prepared in a similar way starting with 4-methyl-4-triethylsilyloxi-1-octyne (Scheme 14). IR ($cm^{-1}$): 1590, 1240, 1060, 860, 840.

EXAMPLE 11

A solution of [(E)-1-(tri-n-butyltin)-4-methyl-4-trimethylsilyloxy]-1-octene (308 mg) in THF (1.1 ml) is cooled under nitrogen to −60° C. and 0.35 ml of 2.05N n-BuLi in hexane are added dropwise and stirred 1 h at −50° C.

After cooling to −60° C., a solution of 1pentinyl Cu(I) (73 mg) and HMPT (0.2 ml) in THF (1.1 ml) is added and stirred for 10 min. Then a solution of protected enone (100 mg) in ether (0.5 ml) is added and stirred for 1 h. Then, a solution of tBDMSiCl (89 mg) and HMPA (1 ml) in ether (0.6 ml) is added and stirred for 45 min at −15° C. The resulting reaction mixture is poured over a saturated $NH_4Cl$ solution and stirred 30 min, extracted with ether (3×15 ml) and washed with cold 0.5N HCl, 2.5% $NaHCO_3$ and brine, dried over anhydrous $Na_2SO_4$ and stripped of solvent to yield 428 mg of an oil which is purified by column chromatography using mixtures of n-hexane-EtAcO as eluent obtaining 91.6 mg (45%) of the protected enol XCIX as an oil. IR ($cm^{-1}$): 1740, 1675.

EXAMPLE 12

A solution of LDA (0.177 mmol) in THF (1.22 ml) is added dropwise over a solution of 64.1 mg of silyl enol ether in 0.5 ml of THF and stirred at −78° C. for 10 min. Then a solution of 34.6 mg of $(PhSe)_2$ in THF (0.5 ml) is added and stirred at −78° C. for 40 min and then at −45° C. (dry ice-acetonitrile bath) for 90 min. The reaction mixture is poured over cold 0.1M HCl and extracted with EtAcO, washed with brine, dried and stripped of solvent to yield 90.9 mg of a yellow oil. After column chromatography (silica gel/hexane:EtACo; 7:1), 60.6 mg of C were obtained. IR ($cm^{-1}$): 1730, 1675, 1570.

A solution of the phenyl selenyl derivative C (60 mg) in EtAcO (2 m l) and THF (1 ml) was oxidized in the presence of $NaHCO_3$ (40 mg) with 30% $H_2O_2$ (50 µl) at 35° C. and stirred for 30 min. The solution was diluted with EtAcO, washed with 5% $NaHCO_3$ and brine, dried and stripped of solvent to give 46 mg (72%) of CI as an oil. IR ($cm^{-1}$): 1725, 1675, 1650.

EXAMPLE 13

To the former compound CI (46 mg) 1.1 ml of AcOH-THF-$H_2O$ 3:1:1 is added and stirred at room temperature for 3 h. The reaction mixture is diluted with EtAcO (10 ml) and brine (15 ml). The aqueous phase is extracted with ether (2×10 ml). The organic layer is washed with 5% $NaHCO_3$ and brine to neutrality, dried and stripped of solvent to give 39.7 mg of a crude oil which is purified by column chromatography (silica gel, hexane-EtAcO) to yield 6 mg of the desired product CII. IR ($cm^{-1}$): 1730, 1720, 1650.

EXAMPLE 14

Magnesium (4.67 g) was suspended in 30 ml of anhydrous ether, 5 ml of benzene and activated with iodine or $Hg_2Cl_2$. A solution of 2-hexanone (10 g) and propargyl bromide 80% in toluene (15.25 g) in 40 ml of anhydrous ether was added dropwise at a rate which produced gentle reflux. After the addition was complete, the reaction mixture was heated under reflux for 3 h and then poured into 150 ml of cold 5% $H_2SO_4$. The aqueous phase is extracted three times with 100 ml of ethyl ether. The organic layer was washed with brine, dried over anhydrous $Na_2SO_4$ and stripped of solvent under reduced pressure to give 11.87 g of crude product. This residue was distilled under vacuum to give 8 g (57%) of product CIII. IR ($cm^{-1}$): 3400, 3300, 2100; bp: 80–82° C. (3 mm Hg).

EXAMPLE 15

A solution of 2.25 g of 1-octyn-4-methyl-4-ol (CIII), and 3.06 g of imidazole in 4.5 ml of anhydrous DMF was treated with 2.97 g of triethylchlorosilane. The mixture was stirred for 24 h at room temperature and then poured into a mixture of ether and water. The organic layer was washed with brine until pH=7, dried over anhydrous $Na_2SO_4$, stripped of solvent under reduced pressure to give 3.88 g of product which was chromatographed over silica gel, using n-hexane as eluent to give 3.4 g (81%) of CIV as a colorless liquid. IR ($cm^{-1}$): 3300, 2100, 1100, 1000, 740, 720.

The trimethylsilyl derivative (XCVII) is prepared in a similar way. IR ($cm^{-1}$): 3300, 2100, 1240, 1160, 1070, 1010, 860, 840; b.p.: 61–62° C., 3 mm Hg.

EXAMPLE 16

To 0.75 g of 4-triethylsilyloxy-4-methyl-1-octyne (CIV), 0.40 g of catecholborane was added. The mixture was heated under nitrogen at 60–70° C. during 4.5 h and then poured into cold water with vigorous stirring. The mixture was extracted with hexane and the hexane solution was extracted five times with 1N KOH to remove the catechol. The hexane solution was then extracted 3 to 4 times with MeOH:$H_2O$:KOH (100:20:35). The extracts were combined, cooled to 5° C. and carefully acidified with 2N HCl. The solution was extracted with ether and the ether extract was washed with water, dried over anhydrous $Na_2SO_4$ and stripped of solvent under reduced pressure to give 0.35 g (39%) of a dark oil (CV). IR ($cm^{-1}$): 1630, 1370, 1100, 1000.

EXAMPLE 17

A solution of 0.35 g of boronic acid (CV) in 2.9 ml of MeOH was cooled to 0° C. and treated with a solution of 0.1 g of NaOH in 0.9 ml of water. A solution of 0.29 g of iodine in 5.8 ml of MeOH was added dropwise to this solution. The mixture was diluted with ether, washed with water, dried over anhydrous $Na_2SO_4$ stripped of solvent under reduced pressure and chromatographed on silica gel with hexane as eluent to give 0.25 g (56%) of a light red product (CVI). IR ($cm^{-1}$): 1600, 1100, 1000, 730, 720.

EXAMPLE 18

A solution of CVI (0.45 g) in 2 ml ether is cooled under $N_2$ to −60° C. and n-BuLi in hexane (1.75 mmol) is added dropwise and stirred for 10 min, then a solution of 1-pentinyl Cu (I) (73 mg) and HMPT (0.56 g) in 2 ml ether is added and stirred at −60° C. for 10 min. Then a solution of XCVI (100 mg) in 1 ml ether is added and the resulting solution stirred for 1 h. Then a solution of TBDMSiCl (0.32 g) and HMPA (3 ml) in ether (2 ml) is added and stirred for 45 min at −15° C. The reaction mixture is poured over a saturated solution of $NH_4Cl$ and stirred for 30 min, extracted with ther, washed with cold HCL, 2.5% $NaHCO_3$ and brine, dried over anhydrous $Na_2SO_4$ and stripped of solvent. The residue is chromatographed to yield XCIX (see example 10).

Forms of Administration

The prostaglandins disclosed in this invention, such as B-407, have useful and specific uterotonic activity. The drugs also has bronchodilating, hypotensive and gastric antisecretory activity. They are active when they are administered "per os" but is necessary, other routes of administration are possible in clinical practice; i.e., vaginal, rectal, transdermal.

For solid oral formulations, prostaglandins of formula (I) are administered together with any of the usual vehicles or commonly used excipients employed in the pharmaceutical industry. Tablets, pills, sugar coated pills and hard or soft gelatin capsules are developed as well as controlled release pills or tablets.

Typical excipients and vehicles useful for this invention are for example: potato or corn starch, saccharose, dextrose, microcrystalline cellulose, silicon dioxide, dicalcium phosphate, alginic acid and arabic gum among others, associated with lubricants such as magnesium stearate; stabilizing and suspending agents as tragacanth gum and jelly and, given the case, diverse flavouring and colouring substances.

Oral liquid formulations with prostaglandins of formula (I) as the active agent are administered either in solution or dispersed, vehiculized in an appropriate liquid media nd complemented with additives, flavouring agents and suspending agents, preservatives, etc., as it is commonly known.

The amount of prostaglandins of formula (I) in the mentioned formulations is variable depending on the desired therapeutic effect and on the route of administration. For the "per os" formulations, the quantity of active agents employed are in the order of 0.1% (prostaglandin/pill).

What is claimed is:
What is claimed is:
1. A compound useful as a precursor in the synthesis of compounds of the formula:

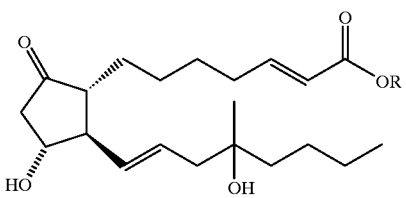

in which R represents $C_1$–$C_4$ alkyl groups of the methyl, ethyl or isopropyl types, represented by the formula:

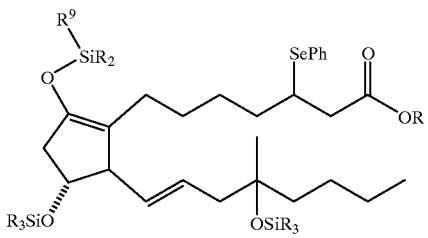

in which R represents $C_1$–$C_4$ alkyl groups of the methyl, ethyl or isopropyl type and $R^9$ represents a bulky alkyl group or an aromatic one.

2. A process for forming the compounds of claim 1, comprising the reaction of compounds of formula:

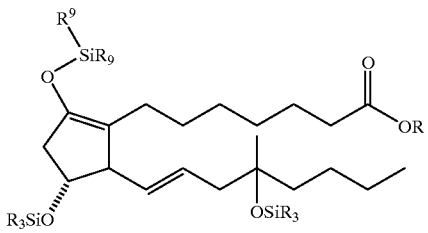

wherein R represents $C_1$–$C_4$ alkyl groups and $R^9$ represents a bulky alkyl group or an aromatic one; with diphenylselenium in the presence of lithium diisopropylamide.

* * * * *